(12) United States Patent
Belley et al.

(10) Patent No.: US 8,286,657 B2
(45) Date of Patent: Oct. 16, 2012

(54) IV CATHETER WITH IN-LINE VALVE AND METHODS RELATED THERETO

(75) Inventors: Richard A. Belley, St. Louis, MO (US); Richard Fiser, Kirkwood, MO (US); Eugene E. Weilbacher, Chesterfield, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 120 days.

(21) Appl. No.: 12/709,861

(22) Filed: Feb. 22, 2010

(65) Prior Publication Data

US 2010/0146765 A1  Jun. 17, 2010

Related U.S. Application Data

(62) Division of application No. 11/546,818, filed on Oct. 11, 2006, now Pat. No. 7,691,090.

(60) Provisional application No. 60/840,367, filed on Aug. 25, 2006, provisional application No. 60/726,026, filed on Oct. 11, 2005.

(51) Int. Cl.
*F16K 43/00* (2006.01)
*A61M 5/00* (2006.01)
*A61M 5/178* (2006.01)
*A61M 31/00* (2006.01)
*A61M 37/00* (2006.01)

(52) U.S. Cl. ............... 137/15.18; 604/245; 604/167.01; 604/93.01

(58) Field of Classification Search ............ 604/246, 604/167.01–167.04
See application file for complete search history.

(56) References Cited

U.S. PATENT DOCUMENTS

| 4,143,853 A | 3/1979 | Abramson |
| 4,424,833 A | 1/1984 | Spector et al. |
| 4,430,081 A | 2/1984 | Timmermans |
| 4,874,377 A | 10/1989 | Newgard et al. |
| 4,895,346 A | 1/1990 | Steigerwald |
| 4,909,798 A | 3/1990 | Fleischhacker et al. |
| 4,917,668 A | 4/1990 | Haindl |
| 4,960,412 A | 10/1990 | Fink |

(Continued)

FOREIGN PATENT DOCUMENTS

WO      WO00/12171      3/2000

OTHER PUBLICATIONS

Corresponding Singapore Application No. 200802635-3 Examination Report, mailed Mar. 31, 2010.

(Continued)

*Primary Examiner* — Nicholas Lucchesi
*Assistant Examiner* — Rebecca E Eisenberg
(74) *Attorney, Agent, or Firm* — Lisa E. Winsor, Esq.

(57) ABSTRACT

Featured is a vascular access device such as an IV catheter device including a housing, a tubular member and a seal member, and a securing mechanism. The housing includes a proximal and distal portion and a chamber that extends between the proximal and distal portions. The tubular member is coupled to the housing distal portion so it is fluidly coupled to the chamber. The seal member is disposed within the chamber and the securing mechanism secures the seal member distal end to the housing proximal portion so the seal member is sealingly and compressibly retained between a chamber proximal end and the securing mechanism. Such a seal member also is constituted so a portion of the seal member moves axially responsive to an axial force applied to the proximal end.

20 Claims, 36 Drawing Sheets

U.S. PATENT DOCUMENTS

| | | |
|---|---|---|
| 5,085,645 A | 2/1992 | Purdy et al. |
| 5,215,538 A | 6/1993 | Larkin |
| 5,242,393 A | 9/1993 | Brimhall et al. |
| 5,322,518 A | 6/1994 | Schneider et al. |
| 5,335,675 A | 8/1994 | Wheeler et al. |
| 5,390,898 A | 2/1995 | Smedley et al. |
| 5,474,536 A | 12/1995 | Bonaldo |
| 5,487,728 A | 1/1996 | Vaillancourt |
| 5,498,247 A | 3/1996 | Brimhall |
| 5,535,771 A | 7/1996 | Purdy et al. |
| 5,535,785 A | 7/1996 | Werge et al. |
| 5,555,908 A | 9/1996 | Edwards et al. |
| 5,562,632 A | 10/1996 | Davila et al. |
| 5,573,516 A | 11/1996 | Tyner |
| 5,676,346 A | 10/1997 | Leinsing |
| 5,738,144 A | 4/1998 | Rogers |
| 5,749,861 A | 5/1998 | Guala et al. |
| 5,776,113 A | 7/1998 | Daugherty et al. |
| 5,788,215 A | 8/1998 | Ryan |
| 5,806,551 A | 9/1998 | Meloul et al. |
| 5,806,831 A | 9/1998 | Paradis |
| 5,817,069 A | 10/1998 | Arnett |
| 5,935,112 A | 8/1999 | Stevens et al. |
| 5,940,661 A | 8/1999 | Yagi et al. |
| 5,954,313 A | 9/1999 | Ryan |
| 5,954,698 A | 9/1999 | Pike |
| 5,967,490 A | 10/1999 | Pike |
| 6,068,011 A | 5/2000 | Paradis |
| 6,068,617 A | 5/2000 | Richmond |
| 6,152,900 A | 11/2000 | Mayer |
| 6,158,458 A | 12/2000 | Ryan |
| 6,171,287 B1 | 1/2001 | Lynn et al. |
| 6,228,060 B1 | 5/2001 | Howell |
| 6,482,188 B1 | 11/2002 | Rogers et al. |
| 6,485,473 B1 | 11/2002 | Lynn |
| 6,699,221 B2 | 3/2004 | Vaillancourt |
| 6,740,063 B2 | 5/2004 | Lynn |
| 6,802,490 B2 | 10/2004 | Leinsing et al. |
| 7,470,254 B2 | 12/2008 | Basta et al. |
| 2005/0043684 A1 | 2/2005 | Basta et al. |
| 2005/0203484 A1 | 9/2005 | Nowak |

OTHER PUBLICATIONS

European Search Report EP08836915.2 dated Sep. 28, 2011.
JP Office Action 2008-535695 dated Oct. 11, 2011.
JP Office Action 2008-535694 dated Oct. 11, 2011.
Australian First Examiner's Report 2006302049 dated Sep. 13, 2011.

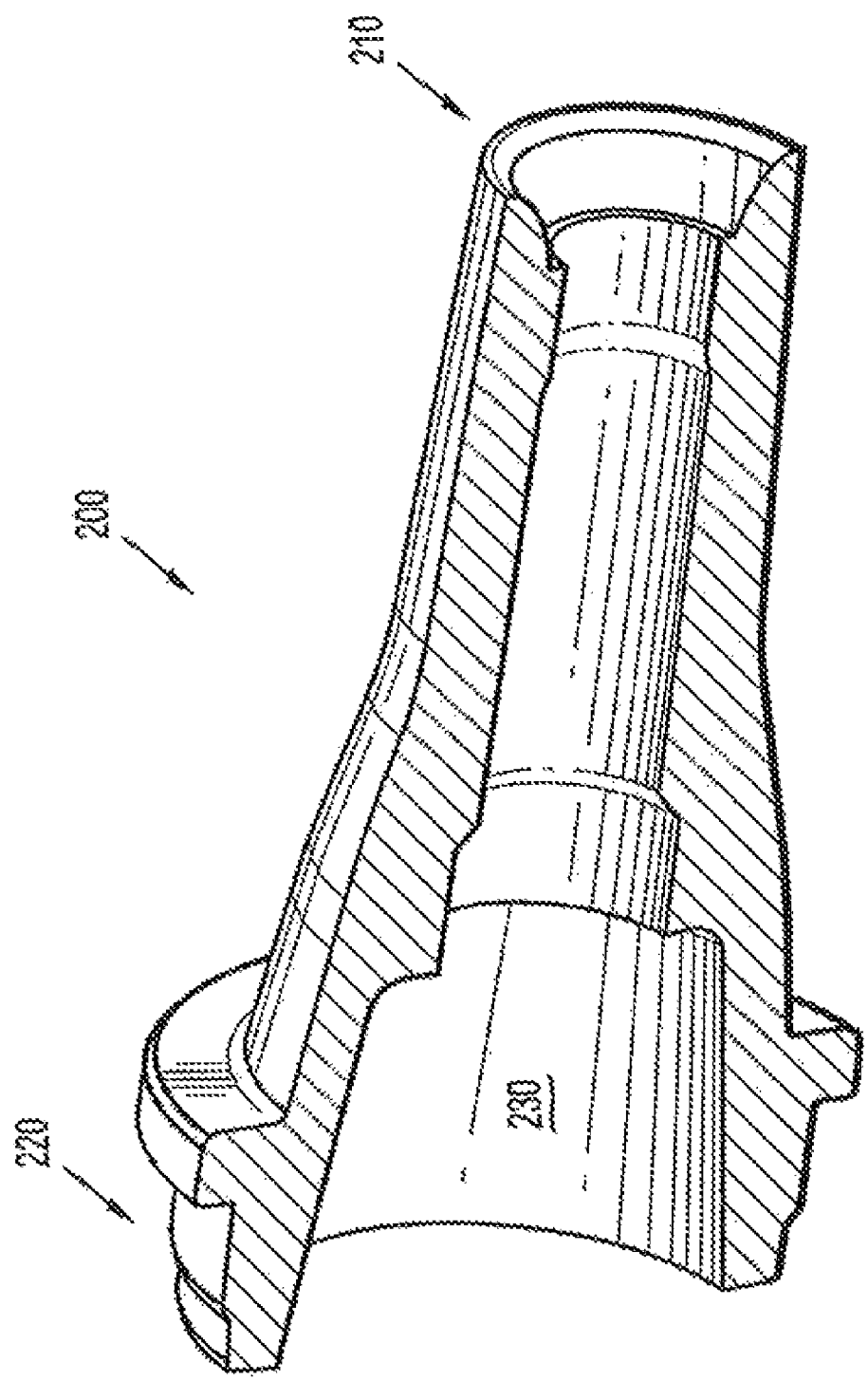

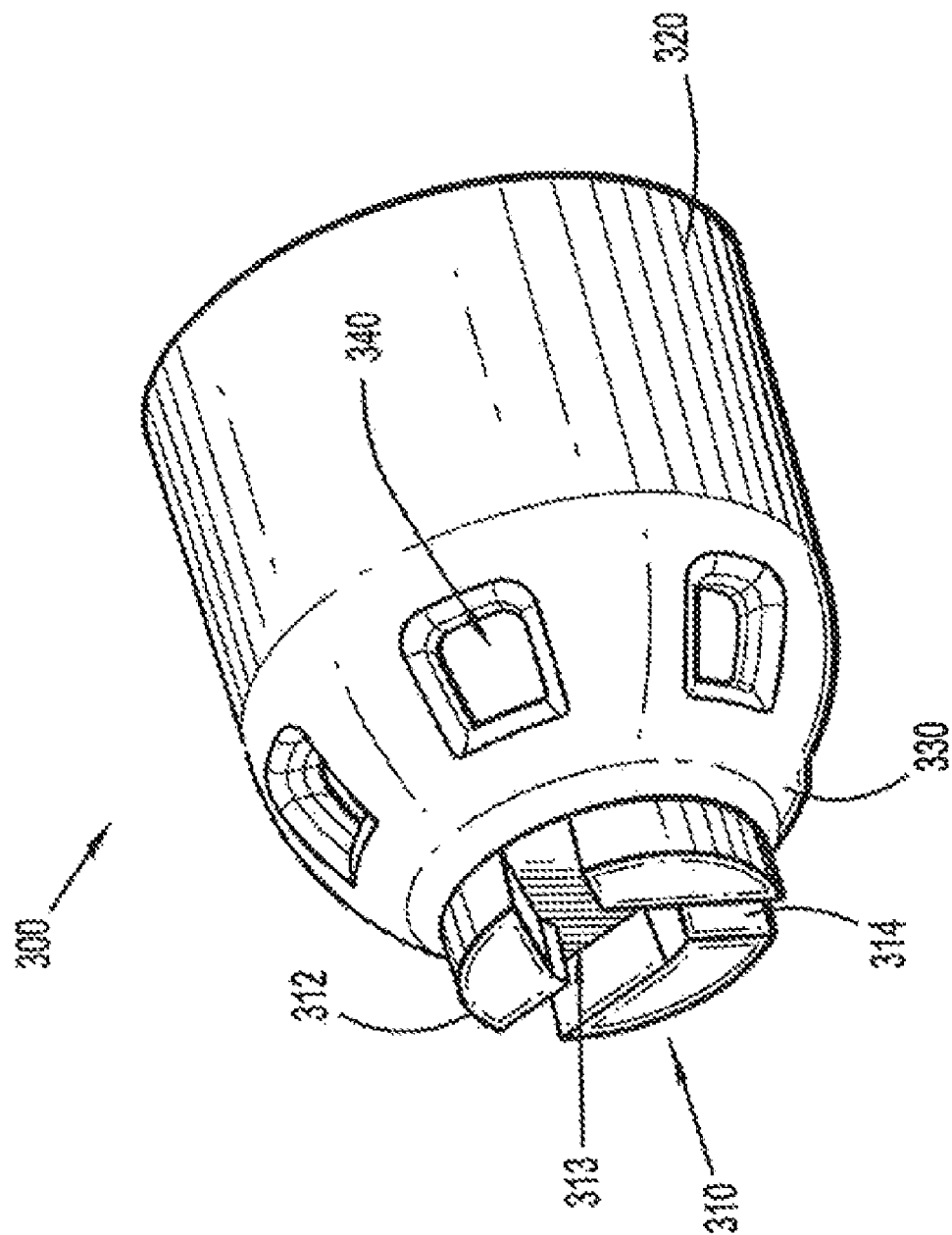

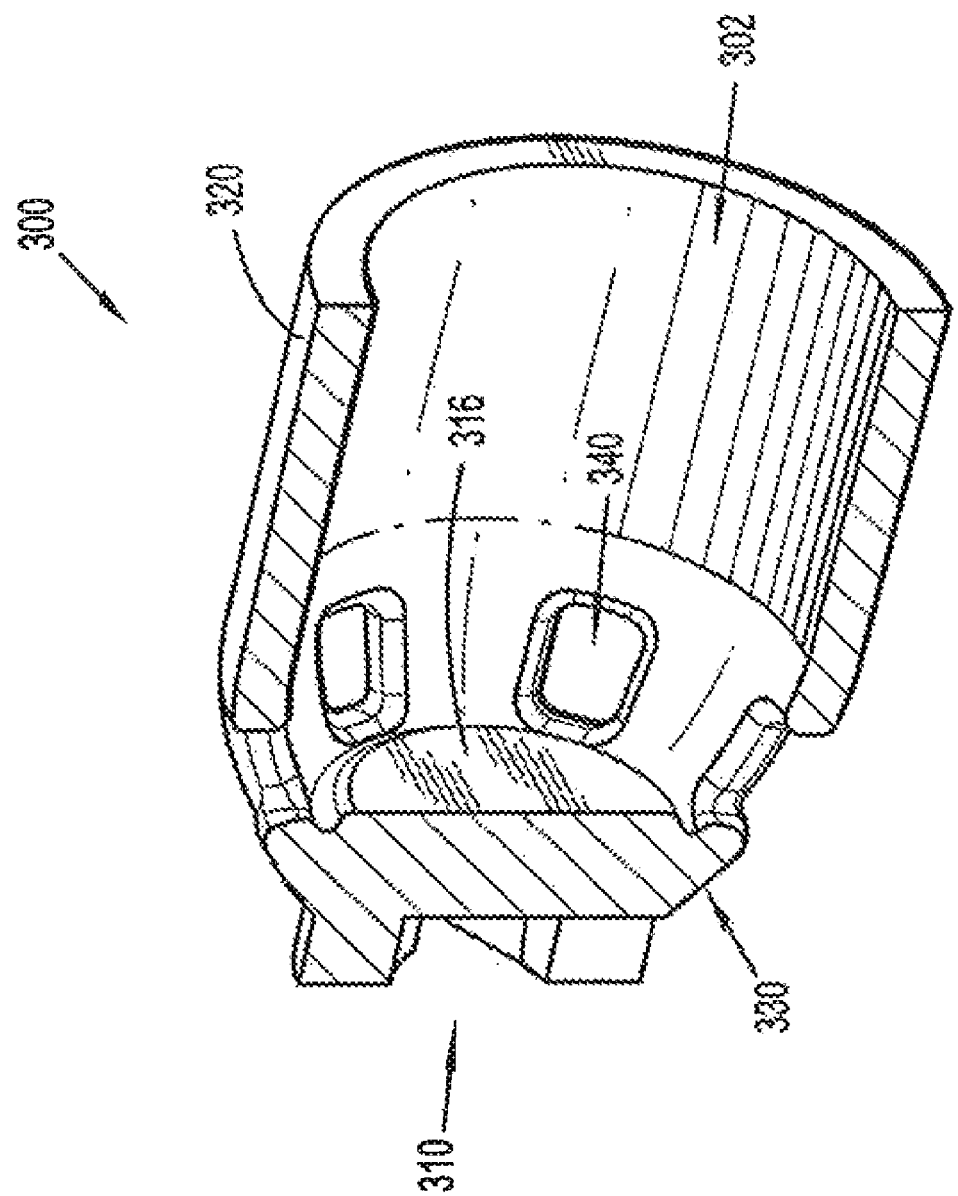

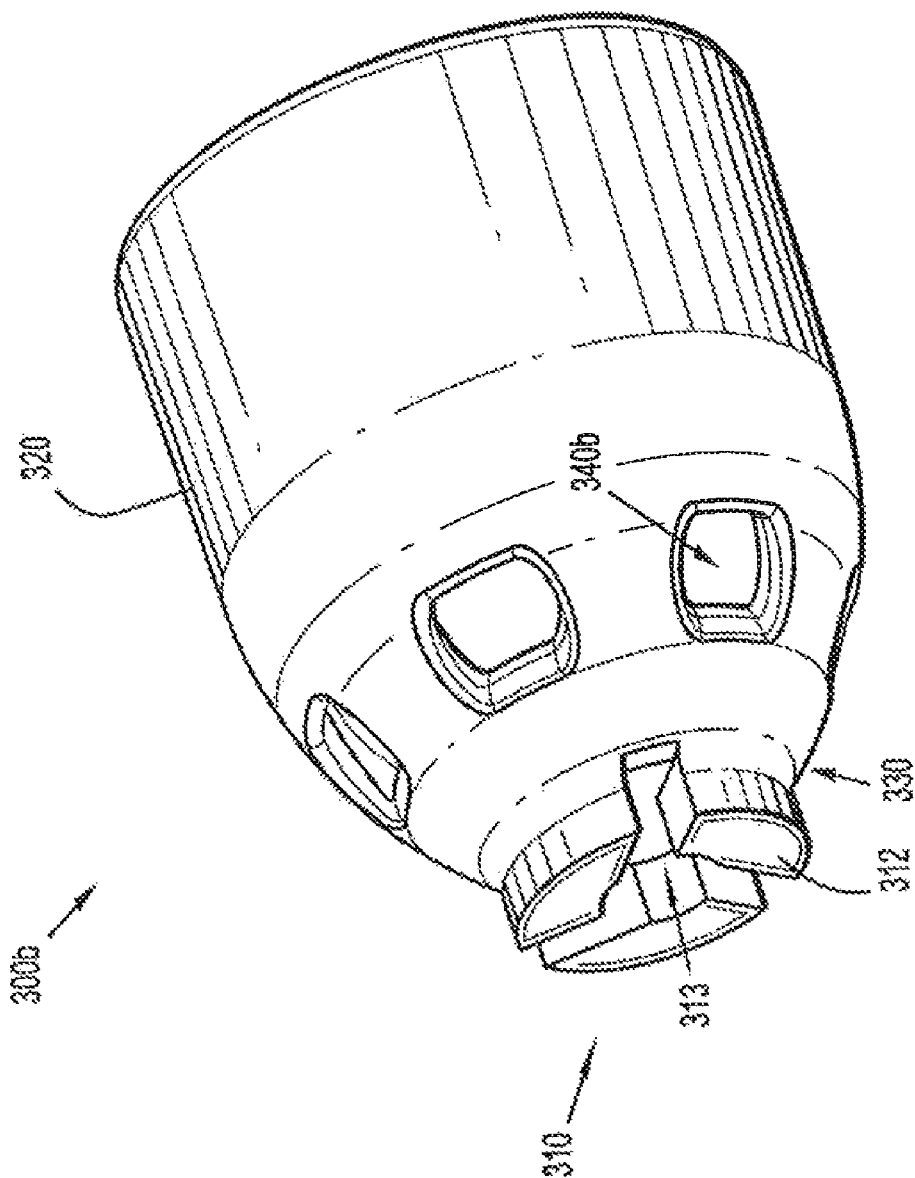

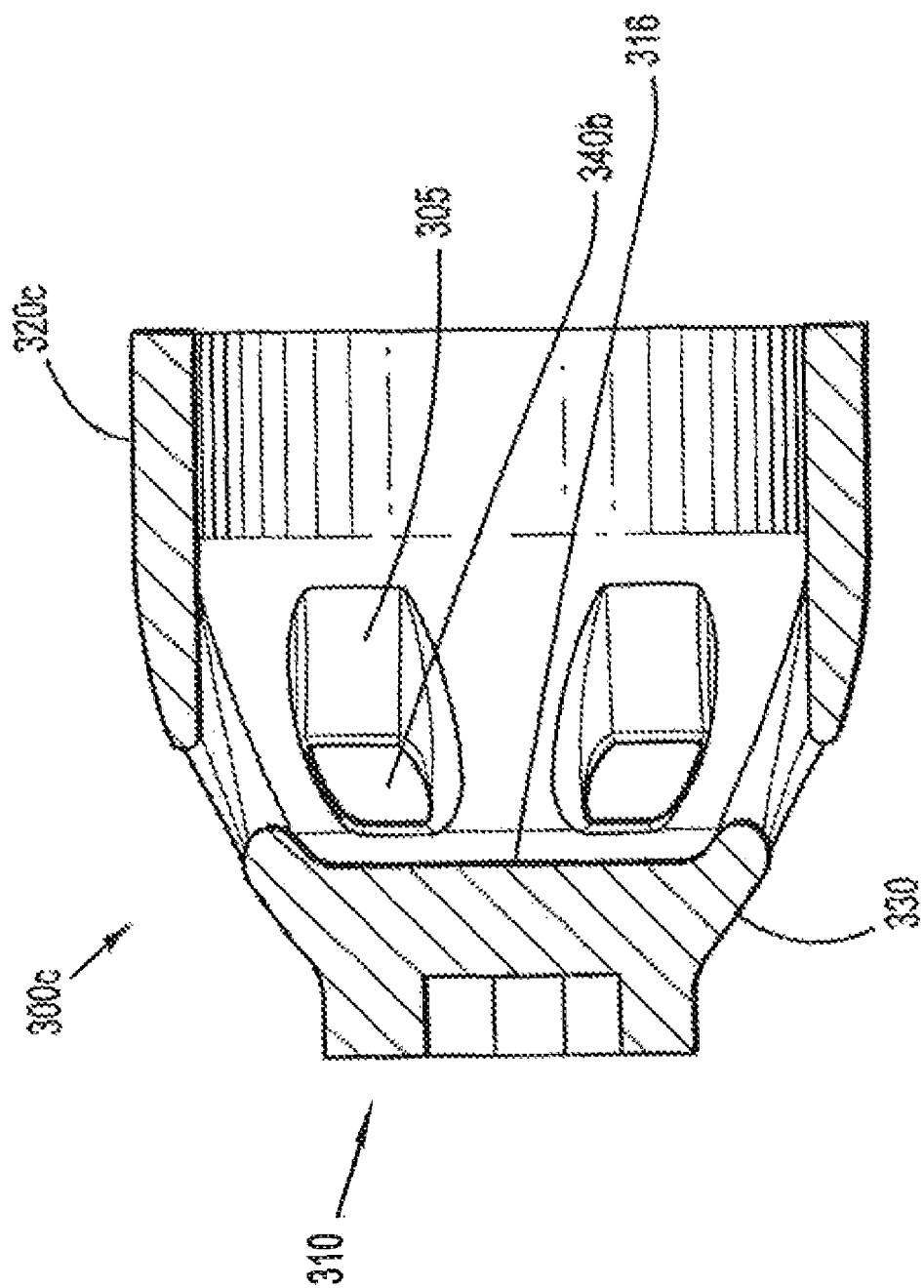

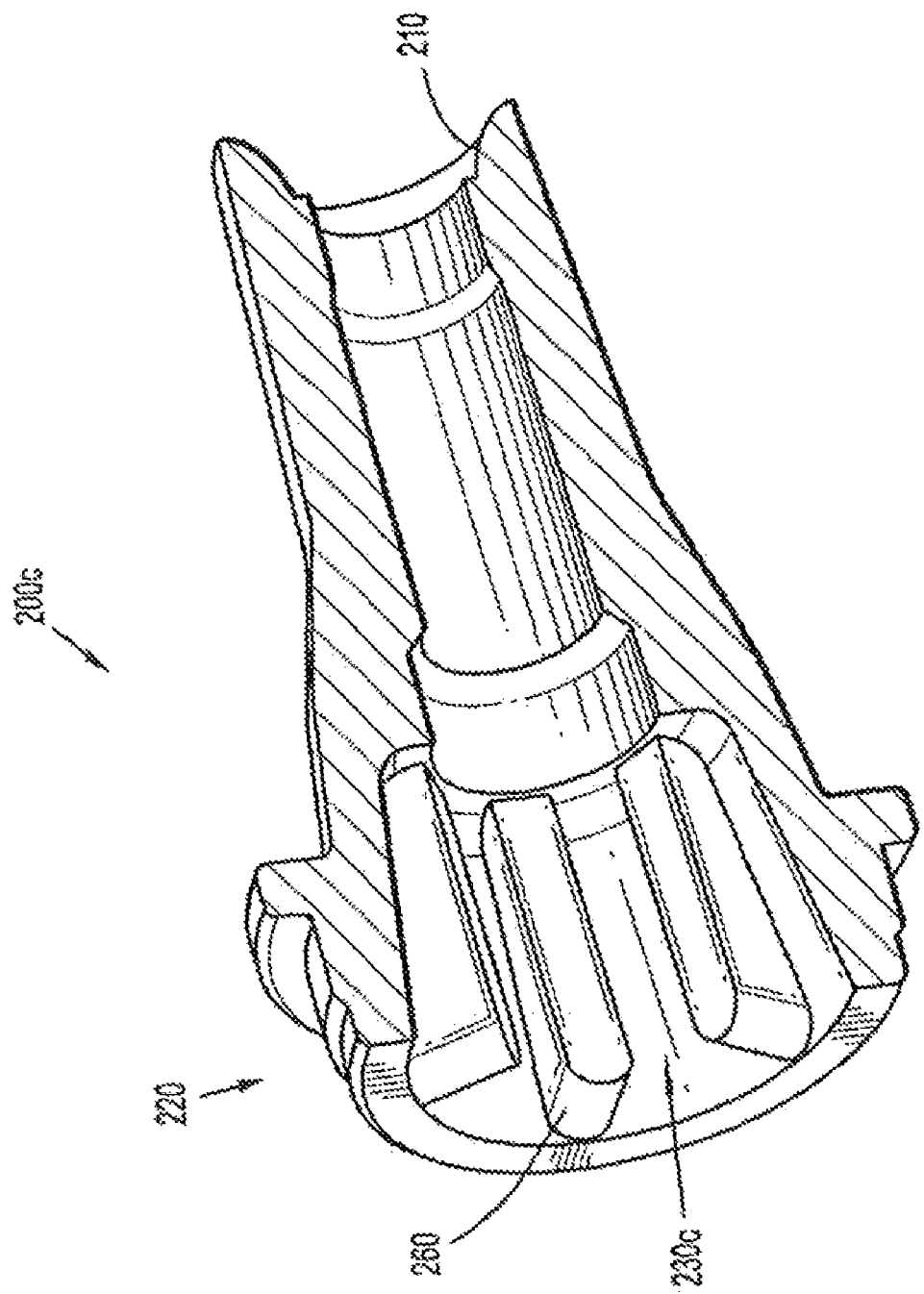

IV CATHETER WITH IN-LINE VALVE AND METHODS RELATED THERETO

CROSS-REFERENCE TO RELATED APPLICATIONS

This application is a Divisional application of U.S. patent application Ser. No. 11/546,818, filed on Oct. 11, 2006, which claims priority from U.S. Provisional Patent Application Ser. Nos. 60/840,367 and 60/726,026, filed on Aug. 25, 2006 and Oct. 11, 2005, respectively, the entire contents of each being incorporated by reference herein.

FIELD OF THE INVENTION

The present invention generally relates to medical infusion or access devices such as intravenous (IV) catheters and more particularly to a vascular access device including a valve and more specifically an over-the-needle IV catheter including an in-line valve and having a re-sealable septum.

BACKGROUND OF THE INVENTION

Medical access devices, particularly infusion devices, over-the-needle catheters, other catheters and feeding tubes, are important tools for administration of fluids to patients. In the normal management of a catheter or other medical access device after it is placed in a patient, it is often necessary to be able to add or withdraw fluids through the device. For example, in surgical procedures, it is a routine practice to place an intravenous catheter so that if it is necessary to medicate a patient during a procedure, the catheter already is in place. It also is common, in post surgical situations or in other types of procedures to see medicaments be periodically administered and/or to see fluid sample(s) withdrawn. For example, an IV catheter may be placed in a patient when a stress test is being performed out of caution as well as when the testing process includes injecting a material into the vasculature for use in a subsequent imaging technique.

Over-the-needle catheters or over-the-needle IV catheters (such as that described in PCT Publication No. 2005-0096592) are used for peripheral intravenous entry into the vasculature of a patient. The disposable medical product is packaged as an assembly of a catheter adapter with its catheter and a needle and hub assembly that are arranged with respect to the catheter adapter so the needle passes through the catheter tube. The needle also extends a slight distance beyond the distal tip of the catheter tube so as to provide a sharpened point for penetration through the skin of the human or animal being catheterized.

After the catheter adapter with its catheter and a needle and hub assembly are inserted into the vasculature or blood vessel of the patient, blood flows due to the vascular blood pressure through the hollow needle and into the hub, sometimes referred to as flashback. Typically, the hub is arranged and configured so the medical personnel are provided a visual indicator of the blood flashback thereby indicating the tip of the needle and thus the distal end of the catheter tube is disposed in the blood vessel. One technique used is constructing the hub at least in part of a transparent material so that the blood flashback is visually apparent to the medical personnel.

According to one prior art technique, when flashback is observed, the practitioner or medical personnel places a finger against the skin of the human or animal and presses against the skin so as to compress the skin and the vessel therebeneath and thereby occlude vessel blood flow proximal to the catheter tip. Such pressing against the vessel is supposed to thereby prevent the flow of blood back through the catheter tube, into the catheter adapter and out onto the patient, bedding, clothing and the like. Thereafter, the needle and hub as an assembly are removed from the catheter (e.g., the catheter hub is held by the clinician as the needle is being pulled).

While efforts are undertaken in this approach to prevent blood flow back through the catheter tube, such efforts are typically not completely effective and some blood flows onto the patient, bedding, clothing and the like. As such, this approach is of some concern because of the possibility of the spread of communicable diseases, particular those such as HIV and Hepatitis. As such, a technique has been developed to minimize exposure to blood whereby the needle and hub assembly is being removed from the catheter and adapter assembly without having to use the hand which positions the patient's arm to also press and stop blood flow. In this other technique, a mechanism is provided that automatically isolates the blood vessel from the open end of the catheter hub thereby preventing blood loss when the needle and hub assembly is and has been separated from the catheter and adapter assembly.

There is described in U.S. Pat. No. 5,085,645 (Purdy et al.), an over-the-needle type of catheter having an adapter including a valve between and in a passage defined in distal and proximal parts of a housing. The described adapter is arranged so as to be an integral part of the catheter hub. In U.S. Pat. No. 5,535,771 (Purdy et al.), there is described a valved adapter for an infusion device.

Others have indicated (see U.S. Pat. No. 5,967,490; Pike) that the device described in U.S. Pat. No. 5,085,645 includes an elongate resilient valve (i.e., its length is greater than its width) having a large internal cavity. Such an elongate valve is believed to be unstable and tends to deflect or travel in a non-linear manner during use, thus creating an unreliable seal, possibly resulting in leakage. Valve leakage can create significant discomfort for the patient and increased risk of infection, along with increased risk of exposure to blood borne pathogens for healthcare workers.

Further, the internal cavity of the prior art device has a tendency to collapse during use as a result of the blood pressure of the patient. This could unseat the valve and produce leakage. Also, the internal cavity results in significant "dead" space in the flow path, in which blood or liquid can get trapped. Such trapped fluids can pose a risk of infection and/or thrombosis to the patient. In addition to the above, an elongate valve results in a longer catheter, which is harder for healthcare workers to use while being more expensive to fabricate.

There is described in U.S. Pat. No. 5,967,698 (Pike) a catheter hub including a housing having a connection end defining a first fluid passageway and a catheter end defining a second fluid passageway. The housing includes a plurality of hub walls arranged in a geometric configuration and which hub walls define a valve chamber. The catheter hub further includes a valve positioned in the valve chamber for controlling fluid flow through the chamber between the first and second fluid passageways and an actuator for actuating the valve. The valve is described as being of a substantially cylindrical configuration and is made of a resilient material. In use, a luer projection contacts the actuator, which in turn causes the valve to move axially within the housing thereby opening the valve. The actuator includes an annular flange that is received in a recess in the valve so as to provide structural support to the valve at the actuator end thereof.

There is described in U.S. Pat. No. 5,954,698 (Pike) a catheter apparatus having a needle protector attached to a catheter hub, which needle protector includes a needle. The catheter hub defines a valve chamber and a valve is positioned in the chamber for controlling fluid flow through the chamber. The valve and catheter hub illustrated therein is the same as that described above for U.S. Pat. No. 5,967,698.

There is described in U.S. Pat. No. 5,817,069 (Arnett) a valve assembly having a body, an end cap, a resilient septum, and an actuator. The body forms a plurality of fluid recesses and the end cap defines a plurality of projections that form channels. The septum is positioned between the body and the end cap. The actuator device is positioned adjacent to the septum so the septum causes the actuator device to be put into sealing engagement with a shoulder defined in the body when in the closed position. When the actuator device is manipulated so the valve assembly is put into the open condition, the actuator device is moved against the septum thereby also moving the actuator device away from the shoulder in the body thereby allowing fluid to pass through the body, actuator, and end cap. The actuator device also is configured with fluid passageways so the fluid flows through the actuator.

There is described in U.S. Pat. No. 5,242,393 (Brimhall et al.) an infusion site for infusing fluids into a patient. The infusion site includes a housing that supports a pre-slit resealable septum, which is held in radial compression in the housing. The housing also accommodates a valve, which is held in tension in the housing and is opened by the insertion of a cannula into the septum. The valve is closed when the cannula is withdrawn. The septum and valve are linked by an elastic member that interacts with the cannula to open and close the valve.

There is described in U.S. Pat. No. 5,788,215 (Ryan) a medical intravenous administration connector including a first coupling member having a female luer, a valve member having a substantially rigid stem and a substantially resilient body with a sealing surface, and a second coupling member having a fluid coupling extending from one end and an internal valve member support. The coupling members are structured to couple to each other with the valve member being biased to a closed position. When assembled, the valve stem extends into the female luer, and the valve body biases the sealing surface against an annular ring in the first coupling member thereby blocking fluid communication. Preferably, vanes are provided in the second coupling member on which the resilient body of the valve sits, with the vanes acting as a centering mechanism for the valve. The valve may be opened for fluid flow through the assembly by coupling a male luer to the female luer of the assembly, or by pressure actuation. Several valve members are disclosed and several structures for mating the first and second coupling members are disclosed.

There is described in U.S. Pat. No. 5,215,538 (Larkin) an in-line valve for a medical tubing set that has a tubular member characterized by an internal annular valve seat and a generally circular rubber-like valve member disposed transversely of the tubular member with its edges fixed relative thereto and with a central portion thereof tensioned into seating engagement against the annular valve seat to normally close the in-line valve. Valve member elements are engageable by a connector as same is assembled to the tubular member to move the valve member off of the valve seat to automatically open the in-line valve.

There is described in U.S. Pat. No. 5,573,516 (Tyner) a needleless connector having a two-part housing with an inlet, an outlet, and a conical chamber therebetween. The conical chamber compressibly receives a resilient conical valve head. The conical valve head includes a stationary base, and a tip portion movably extending into the inlet. The conical valve head is concentrically positioned against the valve seat to form a seal. When the male fitting of a syringe, or some other device, is inserted into the inlet, it pushes a tip portion of the resilient valve head inwardly, so that the valve head is deformed away from the valve seat to break the seal.

It thus would be desirable to provide a new vascular access device such as an IV catheter device including an in-line valve for controlling the flow of fluid in either direction through the vascular access/IV catheter device and methods related thereto. It would be particularly desirable to provide such a device in which the seal member of the valve is sealingly disposed and retained only within a proximal portion of the device. It also would be desirable to provide such a device that is less complex in structure, manufacture and operation as compared to prior art devices. Also it would be desirable that such methods would not require highly skilled users to utilize the catheter device.

SUMMARY

The present invention features a vascular access device such as an IV catheter device as well methods for making and using such vascular access devices/IV catheter devices. More particularly, such a vascular access device includes a housing formed by a proximal portion and a distal portion and including a chamber therein extending between the proximal and distal portions. A tubular member is coupled to the housing distal portion, the tubular member including a lumen therein that is fluidly coupled to the chamber.

Such a vascular access device also includes a seal member and a securing mechanism. The seal member is disposed within the chamber and has a septum, a distal end, a proximal end, and a sealing portion which sealingly engages with at least a region of the housing proximal portion. The securing mechanism secures the seal member distal end to the housing proximal portion. Also, the seal member distal end is proximal to, and not in contact with, the housing distal portion, such that the seal member is sealingly and compressibly retained between the proximal end of the chamber and the securing mechanism.

In another embodiment, the housing proximal portion includes a distal reduced-diameter portion and a widened portion and the chamber has a proximal end at a junction of the reduced-diameter portion and the widened portion. Further, the seal member sealing portion sealingly engages with at least a portion of the junction.

In further embodiments/aspects, the present invention features an over-the-needle IV catheter device through which an object, such as an introducer needle, an insertion needle, an insertion cannula or the like, is removably passed therethrough. Such an IV catheter device includes a housing, a tubular member and a seal member, and a securing mechanism. The housing includes a proximal portion, a distal portion and a chamber therein extending between the proximal and distal portions. The tubular member is coupled to the housing distal portion so a lumen thereof is fluidly coupled to the chamber. The seal member is disposed within the chamber and the securing mechanism secures the seal member distal end to the housing proximal portion such that the seal member is sealingly and compressibly retained between a proximal end of the chamber and the securing mechanism. Such a seal member also is constituted and arranged so a portion thereof, a sealing portion, moves axially in response to an axial force applied to the proximal end. As described further herein, the sealing portion can be thus displaced from the chamber proximal end such that the sealing portion is no longer in sealing engagement with the chamber proximal end.

The seal member also is configured so as to include a septum in which an introducer needle is removably received. In particular embodiments, a portion of the seal member proximal end includes a sealing portion for sealing engagement with at least a portion of the chamber proximal end and the seal member is configured so the septum lies in the same general plane as the sealing portion. In other embodiments, the seal member is configured so that the septum is spaced from the proximal end or the septum is spaced from the sealing portion(s). More specifically, the septum is spaced in a distal direction from the proximal end or the sealing portion (s).

In more particular embodiments, the seal member further includes one or more axially extending walls that extend from the proximal end into the seal member inner cavity. Also, the septum is secured to a common end of the one or more walls so as to form a pocket extending from the proximal end to the septum.

In further embodiments, the seal member further includes a collar portion comprising one or more axially extending walls. Such a collar portion is secured to a bottom surface of the septum so that the one or more axially extending walls extend into the seal member inner cavity. In exemplary embodiments, the collar portion comprises an axially extending annular structure that more specifically forms an integral structure with the septum.

In further embodiments, the seal member proximal end includes a plurality of raised sections, a plurality of channels and a centrally located chamber. The plurality of channels are arranged so as to extend between an outside surface of the raised sections and the centrally located chamber.

In particular embodiments, the securing mechanism is a ring member that is secured to the housing proximal portion using any of a number of techniques known to those skilled in the art. Also, the ring member is secured to the housing proximal portion so that the seal member is sealingly and compressibly engaged between a surface (a top surface) of the ring member and the proximal end of the chamber. In more particular embodiments, the ring member is mechanically secured to the housing proximal portion.

In further embodiments, an inner surface of a portion of the chamber that is in the housing proximal portion is configured so as to include a depression that is located a preset distance from the chamber proximal end. The ring member is mechanically secured within the depression to the housing proximal portion. Such mechanically securing includes one of an adhesive, snap-fit, press-fit, interference fit, welding or other types/forms of known mechanical connections.

In an illustrative exemplary embodiment, the depression comprises a groove provided (e.g., machined, formed, cast, molded) in the inner surface of the chamber portion in the housing proximal portion that is located a preset distance from the chamber proximal end. After the seal member is inserted into the proximal housing, the ring member is manipulated so a portion of the ring member is disposed within the groove thereby forming a mechanical connection between the proximal housing portion and the ring member. More specifically, the groove is arranged so as to have a width that restricts axial or side-to-side movement of the ring member within the groove.

In another illustrative exemplary embodiment, the depression comprises a combination of a lip or shoulder and a rib or step structure in the inner surface. The lip is provided (e.g., machined, formed, cast, molded) in the inner surface of the chamber portion in the housing proximal portion that is located a preset distance from the chamber proximal end. The rib is displaced axially from the lip and extends circumferentially about the inner surface and radially outwardly from the inner surface (i.e., towards a long axis of the distal housing). After the seal member is inserted into the proximal housing, the ring member is manipulated so a portion of the ring member is disposed between the lip and the rib thereby forming a mechanical connection between the proximal housing and the ring member. In further embodiments, the lip and rib are arranged so the spacing therebetween is sufficient to restrict axial or side-to-side movement of the ring member when it is disposed between the lip and rib.

In more particular illustrative embodiments, the rib is configured so as to have a distal side surface extending in a distal direction, the distal side surface being a sloped surface. In further embodiments, the rib includes a proximal side surface having a first portion that is substantially parallel to the vertical surface of the lip and having a second portion that slopes upwardly and distally from the first portion to the top of the rib. The sloped distal side surface and the sloped proximal side surface second portion, among other things facilitate axial movement of the ring member during the insertion process.

In yet further illustrative embodiments, the depression comprises a lip or shoulder that is provided (e.g., machined, formed, cast, molded) in the inner surface of the chamber portion in the housing proximal portion that is located a preset distance from the chamber proximal end. After the seal member is inserted into the proximal housing, the ring member is manipulated so as to be adjacent to or abut the lip. In one embodiment, the inner diameter of the region of the inner surface proximal the lip is arranged so that there is an interference fit between the ring member and the inner surface thereby mechanically engaging the ring member with the inner surface. Alternatively, any of a number of securing techniques known to those skilled in the art is used to mechanically secure the ring member to the proximal housing so as to be adjacent to or abutting the lip.

In further embodiments, the housing distal portion includes a plurality of axially extending fins that extend inwardly from an inner surface of a portion of the inner chamber disposed within the housing distal portion, the fins being arranged so as to create any of a number of structural arrangements known to those skilled in the art and appropriate for the intended use. Such a structural arrangement being such as to form a physical barrier or stop to limit axial movement of the seal member to high pressure flow fluid conditions while maintaining adequate flow area for passage of fluid through the IV catheter in either distal or proximal directions. Such an arrangement also should allow the object (e.g., introducer needle, insertion cannula or the like) to pass through the IV catheter in the intended manner. More particularly, the axially extending fins are arranged so they do not contact the seal member or the securing mechanism (e.g., the ring member) when the IV catheter is in the valve closed or sealed condition/position.

In exemplary embodiments, the plurality of axially extending fins extend radially inwardly from the inner surface so as to form a stop structure that is opposite to the seal member septum and so as to provide a centrally located axially extending open region through which the introducer needle passes as well as an open flow area for the passage of fluid. In other exemplary embodiments, the plurality of axially extending fins extend inwardly from the inner surface in a non-radial fashion so as to form a stop structure that is to the seal member septum and so as to provide a centrally located axially extending open region through which the introducer needle passes.

In yet other exemplary embodiments, the stop structure comprises a grate like structure (e.g., a structure composed of intersecting members that extend chord like across the inner surface of the distal housing. Such intersecting members also are arranged so to form a stop structure that is opposite to the seal member septum and so as to provide a centrally located open region through which the introducer needle passes as well as providing an open flow area for the passage of fluid.

The present invention also features such an over-the-needle catheter device in combination with an introducer needle. This shall not be considered limiting as the IV catheter of the present invention is adaptable for use with any of a number of medical devices or catheters which embody an in-line valve or valve. In particular, the IV catheter of the present invention is adaptable for use with any of a number of medical devices or catheters in which an object is removably passed through the catheter. Also featured are device kits, including an IV catheter of the present invention such as for example, a device including an over-the-needle catheter device embodying an in-line valve IV catheter of the present invention and an introducer needle. According to these aspects of the present invention, the introducer needle or object extends axially within the housing and so as to sealingly pass through the seal member septum of the catheter device.

As well as featuring methods for using such devices, the present invention also features a method for making such in-line valve over-the-needle IV catheter devices. Such methods include the steps of providing a housing proximal portion having an internal cavity, a proximal end and a distal end, where the internal cavity includes a proximal end and providing a housing distal portion having an internal cavity, proximal and a distal end. Such methods also include securing a tubular member to the distal housing such that a lumen of the tubular member is fluidly coupled to the distal housing internal cavity and disposing a seal member having a proximal end and a distal end, where the proximal end includes a sealing portion within the proximal housing internal cavity. Such methods further include securing the seal member distal end to the proximal housing such that the seal member is sealingly and compressibly retained between the proximal end of the proximal housing inner cavity and the ring member. The seal member is secured to the proximal housing and the proximal and distal housings are secured together.

The present invention also features an in-line valve connector, sometimes referred to generally as a needleless connector, for use in fluid connection with medical applications such as with intravenous lines. Such a needleless connector according to the present invention includes a housing, a seal member, and a securing mechanism. The housing includes a proximal portion, a distal portion and a chamber therein extending between the proximal and distal portions. The housing distal portion is configured so as to include a fluid connection that is fluidly coupled to the chamber. The housing proximal portion also is configured so as to include a fluid connection that is fluidly coupled to the chamber. These fluid connections can embody any of a number of connection techniques known to those skilled in the arts, such as for example, luer-type connections.

The seal member is disposed within the chamber and the securing mechanism (e.g., a ring member) secures the seal member distal end to the housing proximal portion such that the seal member is sealingly and compressibly retained between a proximal end of the chamber and the securing mechanism. Such a seal member also is constituted and arranged so a portion thereof, a sealing portion, moves axially responsive to an axial force applied to the seal member proximal end. As described herein, when such an axial force is applied the sealing portion is displaced from the chamber proximal end such that the sealing portion is no longer in sealing engagement with the chamber proximal end.

It is within the scope of the present invention for such an in-line valve connector to embody other aspects, embodiments, and features herein described for the in-line valve IV catheter including adapting such other aspects, embodiments, and features for use in the in-line valve connector.

Other aspects and embodiments of the invention are discussed below.

DEFINITIONS

The instant/present invention is most clearly understood with reference to the following definitions:

The term "co-planar septum" shall be understood to mean a septum that is located essentially on the same axial plane as the seat area.

The term "proximal" shall be understood to mean or refer to a location on the device object or part being discussed which is closest to the medical personnel and farthest from the patient in connection with whom the device is used when the device is used in its normal operation.

The term "distal" shall be understood to mean or refer to a location on the device, object or part being discussed which is farthest from the medical personnel and closest to the patient in connection with whom the device is used when the device is used in its normal operation.

The term "medical personnel" shall be understood to be generally inclusive of clinicians, surgeons, medical technicians, lab technicians, nurses and the like.

The term "patient" shall be understood to include both human and animals and also shall be inclusive of humans or animals that are undergoing medical procedures including but not limited to surgical procedures and diagnostic procedures, medical treatments and/or other techniques/procedures/treatments performed in hospitals, clinics, doctor's offices, diagnostic facilities/laboratories or the like.

BRIEF DESCRIPTION OF THE DRAWING

For a fuller understanding of the nature and desired objects of the present invention, reference is made to the following detailed description taken in conjunction with the accompanying drawing figures wherein like reference characters denote corresponding parts throughout the several views whenever possible and wherein:

FIGS. 4A-G are various views of some illustrative embodiments of the seal member embodied in an in-line valve IV catheter of the present invention;

DESCRIPTION OF THE PREFERRED EMBODIMENT

Figure 1:
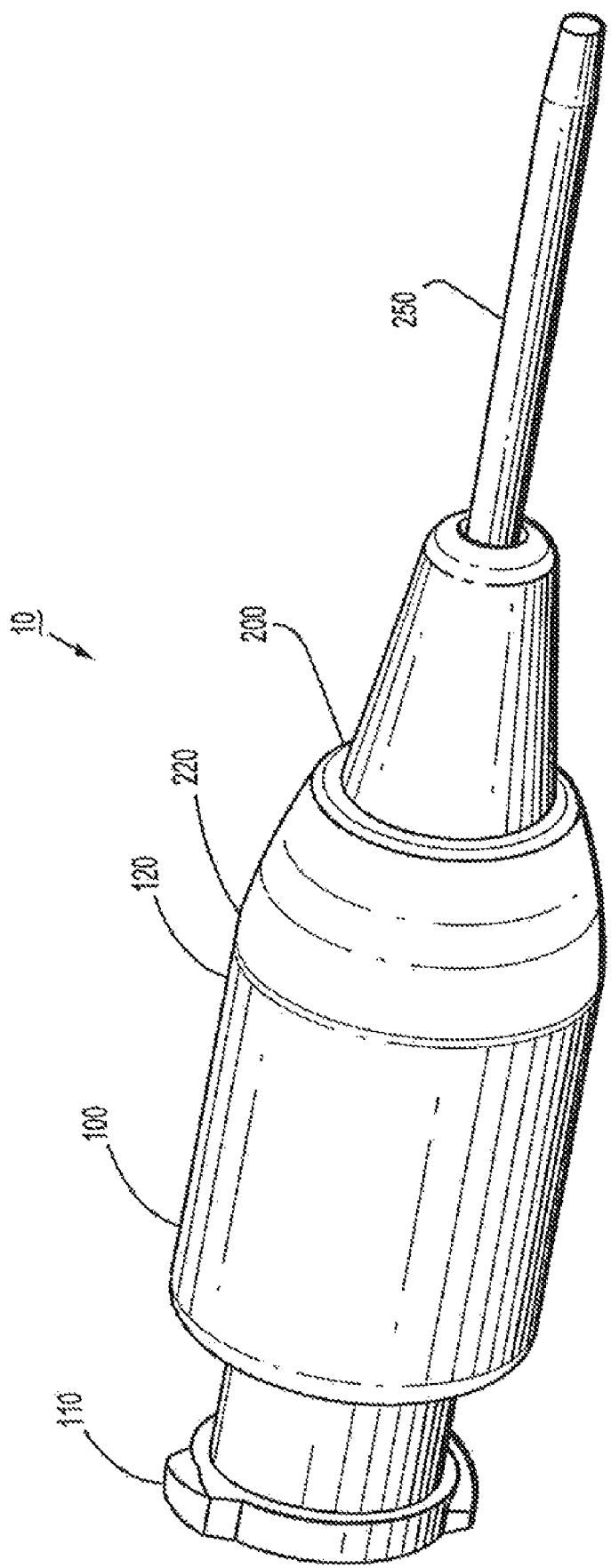
FIG. 1 is an axonometric view of an in-line valve IV catheter.

Referring now to the various figures of the drawing wherein like reference characters refer to like parts, there is shown in FIG. 1 an axonometric view of an in-line valve IV catheter assembly 10 that is of the catheter over stylet/sharp/cannula type of IV catheter. As is more clearly illustrated in FIG. 2A, the stylet/sharp/cannula 20 is inserted through the IV catheter assembly or IV catheter so that the piercing end 22 of the stylet/sharp/cannula 20 extends out of the open end 252 of the catheter tubular member 250. In this way and as known to those skilled in the art, a user inserts the piercing end 22 of the stylet/sharp/cannula 20 through the skin and subcutaneous tissue of the body so that the open end 252 of the tubular member 250 of the IV catheter assembly 10 is disposed within the blood vessel (e.g., vein or artery) of the patient Referring to FIGS. 1A and 1B, cannula 20 preferably includes a proximal end 22a opposite distal end or piercing end 22. Proximal end 22a preferably includes a taper or chamfer 22b which will be described in further detail below. A window or transparent portion 22c may also be provided to view flashback.

Referring now to FIG. 1, the in-line valve IV catheter assembly 10 includes a proximal housing 100 and a distal housing 200 that are secured to each other so as to form an integral unit and so as to form a pressure boundary. Although not shown in FIG. 1 (e.g., see FIG. 2A) such an in-line valve IV catheter assembly 10 also includes a seal member 300 and a ring member 400 that sealingly secures the seal member within the proximal housing (i.e., in the sealing configuration). When in a valve closed configuration, at least a portion of the seal member 300 sealingly engages some inner surfaces of the proximal housing 100 thereby preventing fluid flowing in either proximal or distal directions through the in-line valve IV catheter assembly 10. When fluid flow in either direction through the in-line valve IV catheter 10 is desired (i.e., the valve open configuration), the seal member 300 is manipulated so said at least a portion of the seal member in sealing engagement with inner surfaces of the proximal housing 100 is displaced from these inner surfaces. As is more particularly described herein, such displacement establishes an open fluid flow path within the proximal housing in either the proximal or distal directions.

The distal and proximal housings 100, 200 are constructed of any of a number of bio-compatible materials known to those skilled in the art, including bio-compatible plastics. Also, the proximal and distal housings are secured to each other using any of a number of techniques known in the art including adhesives, mechanical connections, welding (e.g., ultrasonic welding) and brazing techniques that are appropriate for the materials the housings are constructed from. In particular embodiments, the proximal and distal housing 100, 200 are configured so that an end of the one housing (e.g., mating end 220 of the distal housing) is received within the end of the other housing (e.g., mating end 120 of the proximal housing). Also, in further embodiments, the proximal and distal housings are constructed of a bio-compatible plastic and the proximal and distal housings are secured to each other using ultrasonic welding or adhesives.

A coupling end 110 of the proximal housing 100 is generally configured so as to be removably coupled to an external device (not shown) such as syringe, IV drip, IV pump or the like so as to allow a fluid sample(s) to be removed from the patient via the IV catheter assembly 10 or so fluid can be injected into the patient via the IV catheter assembly. In particular illustrative embodiments, the proximal housing coupling end 110 is configured to form a luer lock type end connection as is known to those skilled in the art, although the end connection can be any of a number of connections known or hereinafter developed that is appropriate for the intended use. It also should be recognized that such fluid being injected also can contain or be adapted or be adjusted so as to include any of a number of medicaments, drugs, antibiotics, pain medication and the like as is known to those skilled in the art for treatment and/or diagnosis.

Now referring to FIGS. 2A-6C there are shown various views of an in-line valve IV catheter assembly 10a according to one aspect and components or features thereof. Such an in-line valve IV catheter assembly 10a includes a proximal housing 100a, a distal housing 200, a seal member 300 and a securing or locking ring member 400 (hereinafter generally referred to as the ring member 400). Reference shall be made to the foregoing discussion of the proximal and distal housings 100, 200 of FIG. 1 for further details of the proximal and distal housings 100a, 200 not otherwise described below.

Figure 2A:
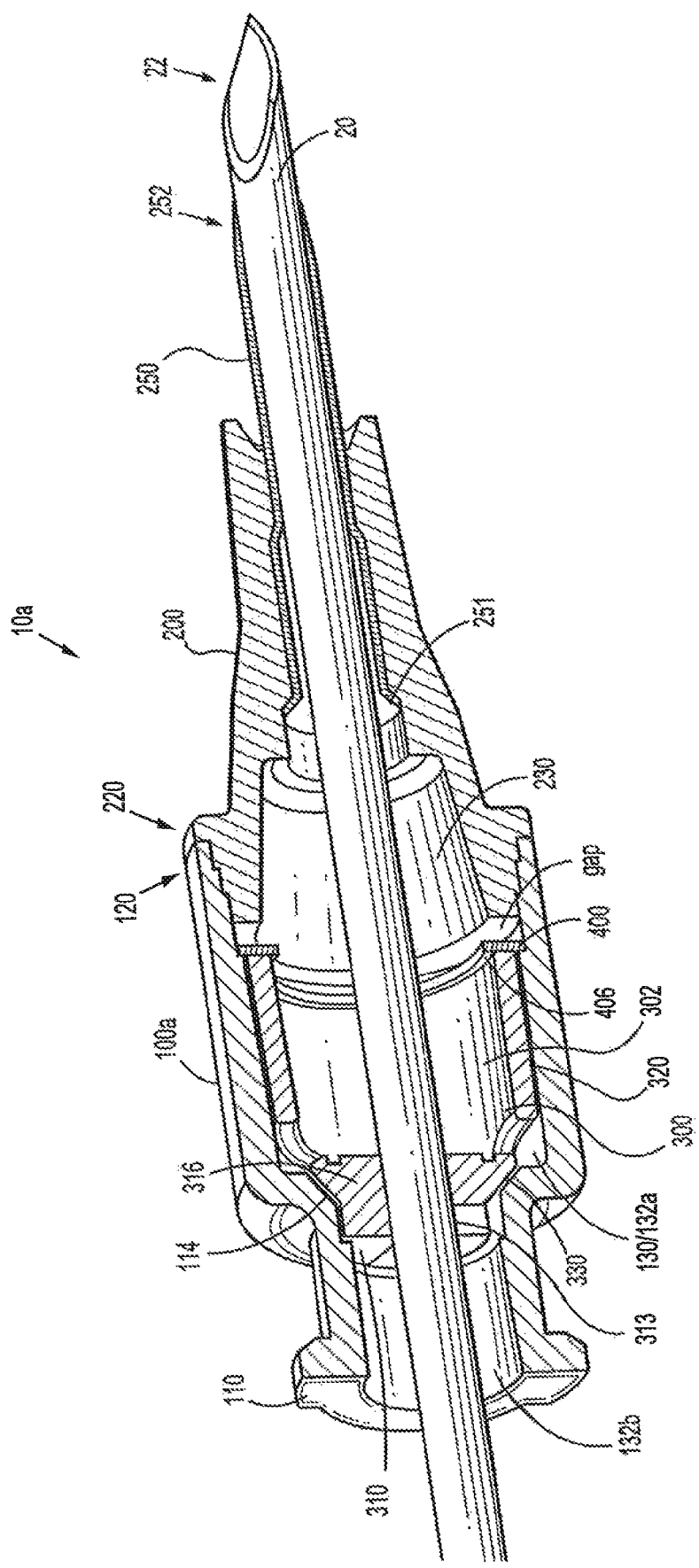
FIG. 2A is a cross-sectional isometric view of one aspect of an in-line valve IV catheter with an object such as an introducer needle or insertion cannula inserted therethrough.

As more particularly illustrated in FIGS. 2A,B when the proximal and distal housings 100a, 200 are joined to each other to form the pressure boundary body of the IV catheter assembly, the most forwardly extending surfaces of the distal housing 200 are spaced from the ring member 400 (i.e., there is a gap between the distal housing and the ring member). As such, no part of the distal housing 200 acts on or applies a force to the seal member 300 so as to thereby cause the seal member to be put into sealing engagement with some inner surfaces of the proximal housing 100a. As described hereinafter, such sealing engagement results from the compression of the seal member 300 by the ring member 400 when the ring member is secured to the proximal housing 100a at a predetermined location within the proximal housing.

In exemplary, illustrative embodiments, the seal member 300 is a bell shaped member (e.g., see FIGS. 4A,B). Other shapes, however, can be utilized and thus are contemplated which other shapes are generally characterized as being capable of exhibiting or achieving the herein described mechanical and sealing characteristics for the seal member 300. The seal member 300 also is constructed of a generally resilient material (e.g., an elastomeric material) that allows at least a portion of the seal member to be compressed and/or axially moved along its long or longitudinal axis as herein further described. It should be recognized the foregoing shall not be construed as being limiting as it is contemplated that the seal member can be constituted of materials having different characteristics including different structural or flexibility characteristics.

Such a seal member 300 (e.g., see FIG. 2B) includes a proximal end 310, a distal portion 320, a sealing portion 330, an inner cavity 302 and one or more of windows 340 or through apertures. In more particular embodiments, the seal member 300 includes a plurality of such windows 340. As described herein in more detail, such compression or axial movement occurs when an axial force is applied to the proximal end 310 of the seal member 300 such as for example a portion of the coupling device being removably coupled to the coupling end 110 of the proximal housing 100a.

Referring also to FIGS. 3A-3D, the proximal housing 100a is configured so as to include an inner cavity 130 that extends along a long or longitudinal axis of the proximal housing 100a from the mating end 120 to the coupling end 110 of the proximal housing. Similarly, the distal housing 200 includes an inner cavity 230 that extends along a long or longitudinal axis of the distal housing from the mating end 220 thereof to a distal end 210 thereof.

As more clearly illustrated in FIG. 2A, a portion of the distal housing inner cavity 230 is configured so it receives the tubular member 250 therein and so that the tubular member is secured to the distal housing 200. Such securing can be accomplished using any of a number of techniques known to those skilled in the art and which are appropriate for the materials of the distal housing 200 and tubular member 250. In illustrative embodiments, a wedge element 251 is used to secure the tubular element 250 to the distal housing in which the insertion of the wedge element causes the tubular element to expand outwardly into mechanical engagement with the distal housing. Alternatively, the tubular member 250 is secured within the distal housing an adhesive. In addition, the tubular member 250 is secured within the distal housing inner cavity 230 and both the distal housing 200 and the tubular member are configured so the inner cavity and tubular member cooperate to form a continuous fluid/pressure barrier from the mating end 220 of the distal housing 200 to the open end 252 of the tubular member 250.

Figure 3A:
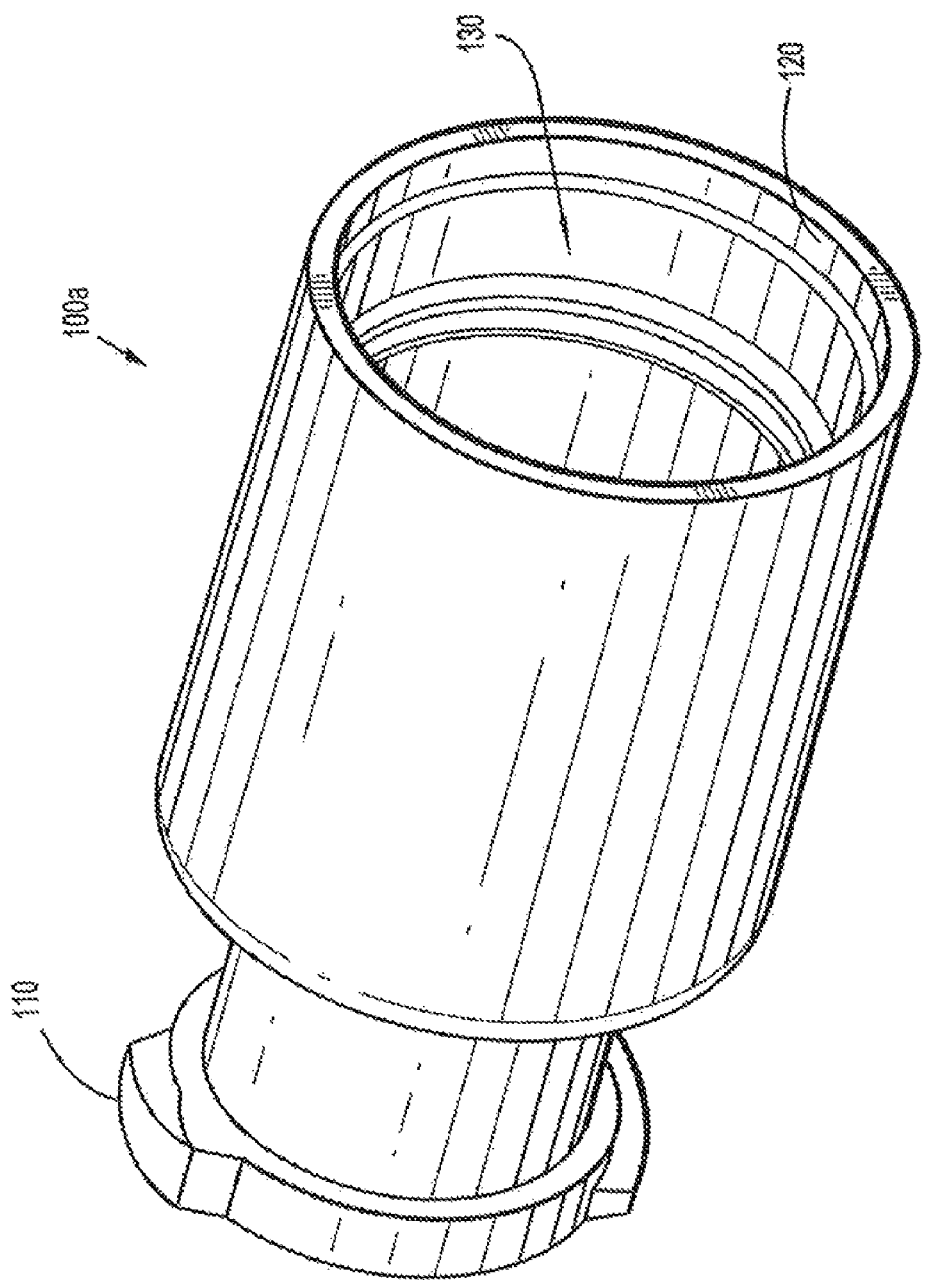
FIGS. 3A, B are various views of the proximal housing of the in-line valve IV catheter of FIG. 2A.

The proximal housing inner cavity 130 includes a first portion 132a and a second portion 132b, the second portion being fluidly coupled to the first portion (FIGS. 3A, B). The inner cavity first portion 132a is configured so a proximal end thereof includes a seating surface 114 (FIG. 3B) and so a groove 140 is provided in the inner surface of the inner cavity first portion. The first and second portions are fluidly coupled at the proximal end of the first portion. The groove 140 is configured so as to extend circumferentially about the inner cavity/long axis of the proximal housing 100a.

Figure 3B:
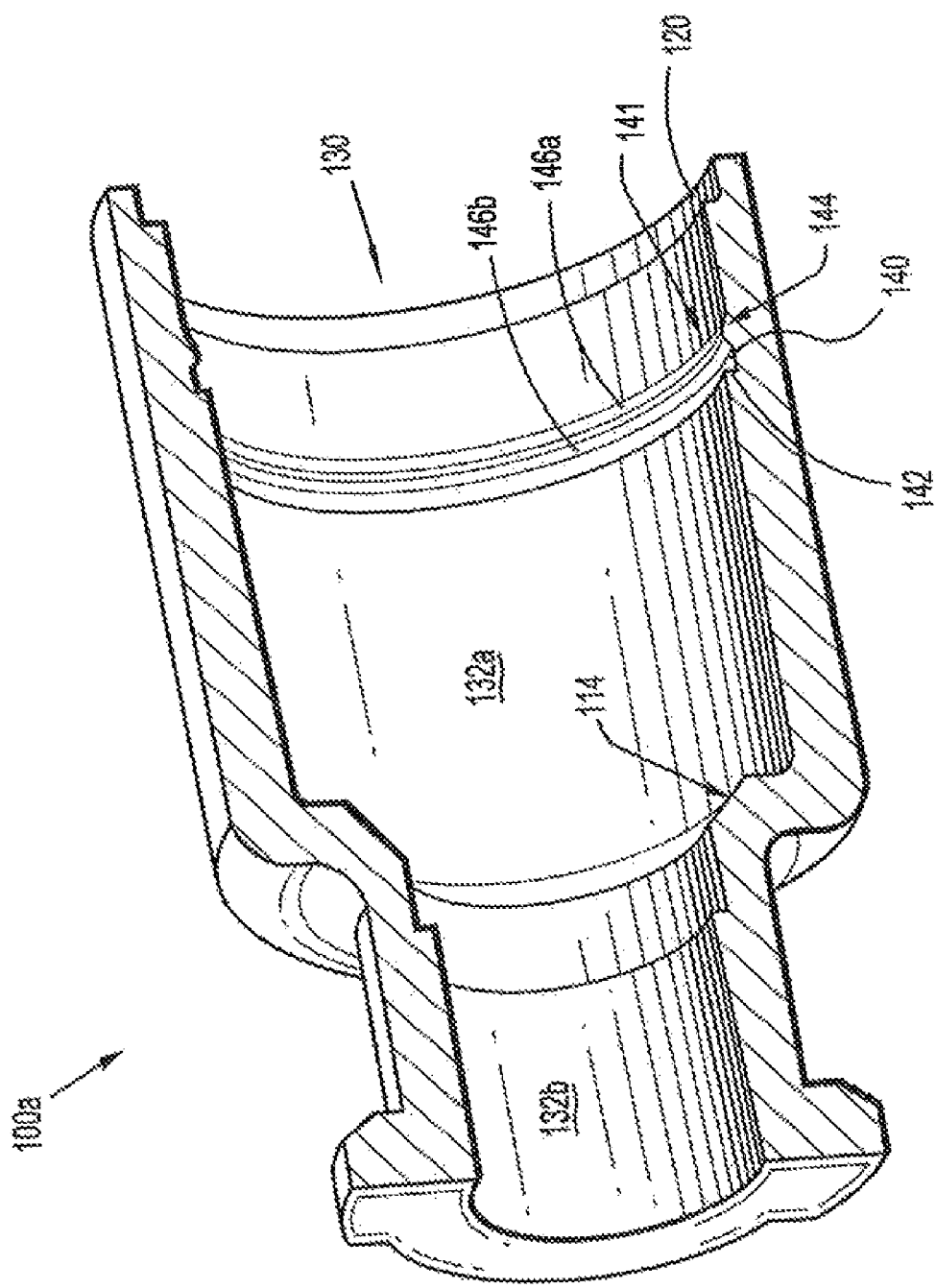
FIGS. 3C, D are various views of the distal housing of the in-line valve IV catheter of FIG. 2A.
Figure 3C:
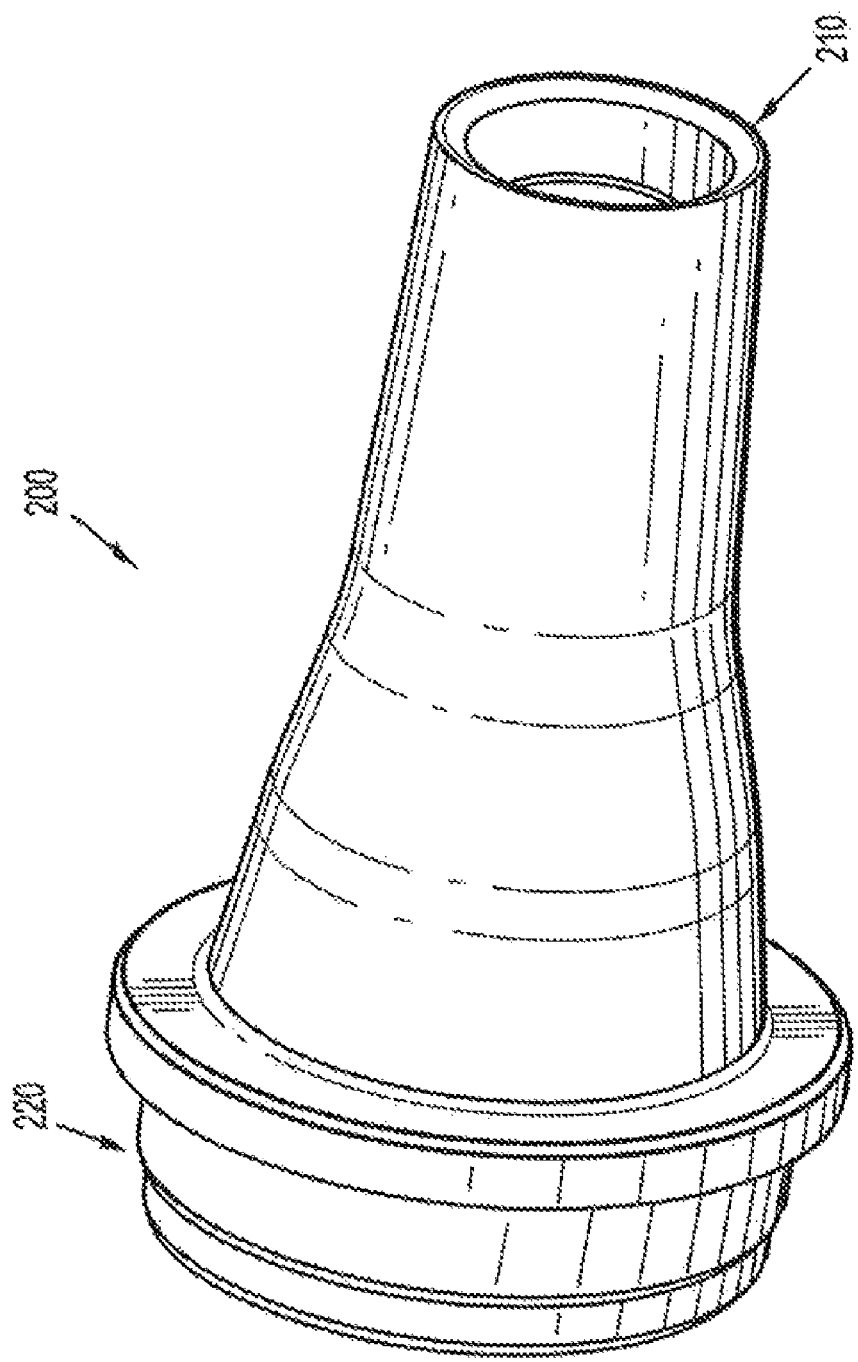

In more particular embodiments, the inner surface of the proximal housing is configured or arranged such that the groove 140 is made up of a lip or shoulder 142 (FIG. 3B) and a step structure or rib 144 (FIG. 3B). The lip or shoulder 142 lip is provided (e.g., machined, formed, cast, molded) in the inner surface of the proximal housing 100a so the shoulder is located a preset distance from the proximal end or seating surface 114 of the proximal housing. The rib 144 is displaced axially in the distal direction from the shoulder 142 and extends circumferentially about the inner surface and radially outwardly from the inner surface (i.e., towards a long axis of the distal housing). The shoulder 142 and rib 144 are configured (e.g., spacing from each other and depth/height) so as to receive and hold the ring member 400 (FIG. 2A) in the region between the shoulder and rib so the ring member is in effect secured to the proximal housing 100a. In further embodiments, the lip 142 and rib 144 are arranged so the spacing therebetween is sufficient to restrict axial or side-to-side movement of the ring member 400 when it is disposed between the shoulder 142 and rib 144. In this way, the ring member 400 is maintained in fixed relation to the seating surface 114 of proximal housing 100a.

In more particular illustrative embodiments, the rib 144 is configured so as to have a distal side surface 146a (FIG. 3B) extending in a distal direction. The distal side surface is a sloped surface downwardly (i.e., in a direction away from the long or longitudinal axis of the proximal housing) and in a distal direction (i.e., towards the proximal housing mating end 120). Also, the rib 144 includes a proximal side surface 146b (FIG. 3B). In one embodiment, the rib proximal side surface 146b is arranged so it is substantially parallel to the opposing surface of the shoulder 142. In another embodiment, the rib proximal side surface 146b is arranged (as shown in FIG. 3B) so as to be sloped upwardly towards the long axis of the proximal housing and in a distal direction. The foregoing is not limiting but intended to be illustrative of possible configurations for the rib 144 and the associated side surfaces 146a,b. The sloped distal side surface 146a also is preferably configured to, among other things, facilitate axial movement of the ring member 400 during the insertion process.

In yet further illustrative embodiments, the inner surface of the proximal housing 100a is configured or arranged such that a shoulder 142 (FIG. 3B) is provided (e.g., machined, formed, cast, molded) in the inner surface of the proximal housing 100a and which is located a preset distance from the proximal end or seating surface 114 of the proximal housing. In this embodiment, after the seal member 300 is inserted into the proximal housing, the ring member 400 is manipulated so as to be adjacent to or abut the shoulder 142. In one embodiment, the inner diameter of the proximal housing in the region of the inner surface proximal the shoulder 142 is arranged so that there is an interference fit between the ring member 400 and the inner surface thereby mechanically engaging the ring member 400 with the proximal housing 100a. Alternatively, any of a number of securing techniques known to those skilled in the art is used to mechanically secure the ring member 400 to the proximal housing 100a so it is adjacent to or abutting the shoulder 142.

Figure 2B:
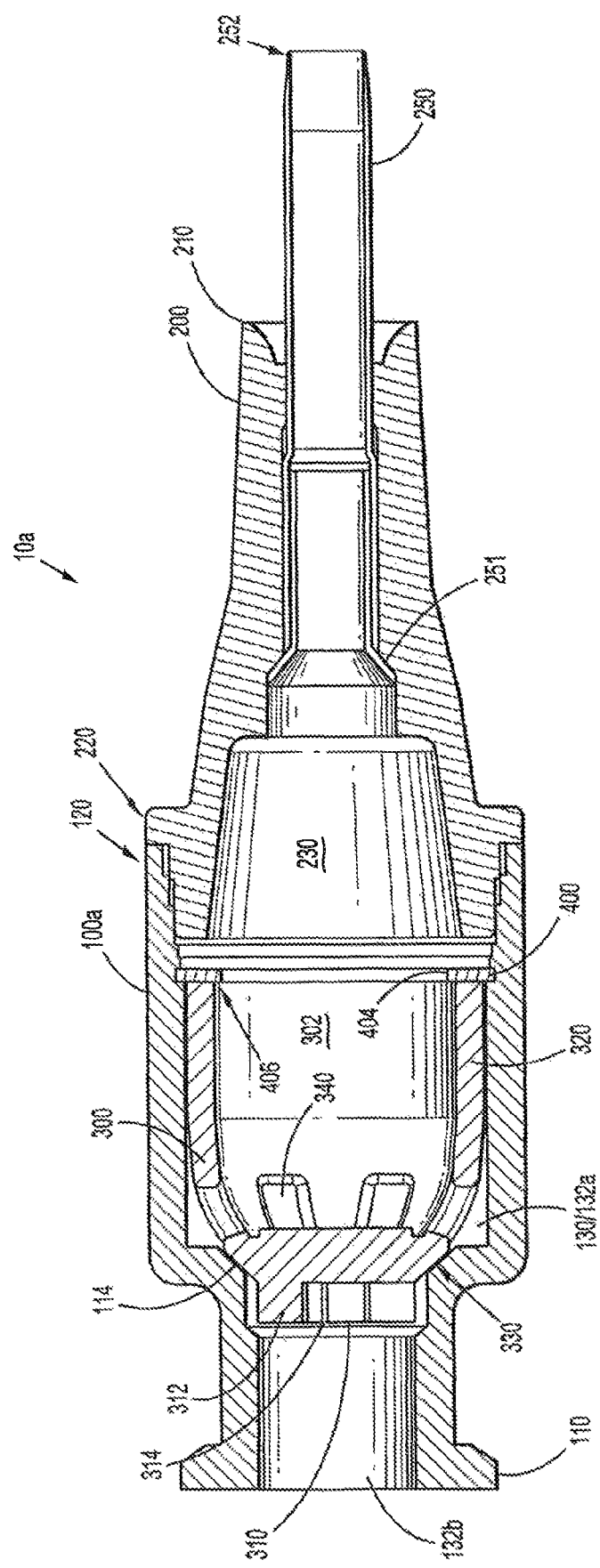
FIG. 2B is a cross-sectional view of the in-line valve IV catheter of FIG. 2A with the object/needle/cannula removed for clarity.

This predetermined distance from the seating surface 114 also is set so that when the ring member 400 is disposed in the groove 140, the seal member 300 is generally compressibly and mechanically retained within the proximal housing 100a between the end of the first portion including the sealing surface 114 and the ring member 400, more particularly, the surface 406 (FIG. 5) of the ring member upon which the seal member 300 rests/abuts. This predetermined distance also is set so that this compressible and mechanical retaining puts the sealing portion 330 of the seal member 300 into sealing engagement with the seating surface 114 of the proximal housing 100a. As described further herein, the proximal end 310 of the seal member 300 does extend past the proximal end of the inner cavity first portion 132a and into the inner cavity second portion 132b as illustrated in FIG. 2B.

The inner diameter of a section of the inner cavity first portion 132a, the section in which the seal member 300 is located, also is set so there is a close fit between the distal portion 320 of the seal member and the opposing surfaces of the inner cavity first portion 132a. In further embodiments, the inner diameter of this section of the inner cavity first portion 132a is set so the distal portion 320 of the seal member 300 is in contact with the opposing surfaces of the inner cavity first portion 132a. In addition, this inner diameter is set so that when the at least some portion of the seal member sealing portion 330 is displaced from the seating surface 114, the seal member distal portion 320 is put into mechanical and sealing engagement with the opposing seating surface within the inner cavity first portion 132a.

In yet further embodiments, this inner diameter is set so that when the seal member 300 is compressibly and mechanically retained within the proximal housing 100a between the proximal end of the inner cavity first portion 132a (i.e., end that includes the seating surface 114) and the ring member 400, the seal member distal portion 320 is maintained in mechanical and sealing engagement with the opposing seating surface within the inner cavity first portion 132a. With these above-described configurations, the pressure tight housing created when the proximal housing 100a and the distal housing 200 are joined and the cooperation of the seating surface 114, the sealing portion 330 of the seal member 300 and the ring member 400 combine to form a structure that functions like a valve.

In yet further embodiments, this inner diameter is set so that when the seal member 300 is compressibly and mechanically retained within the proximal housing 100a between the proximal end of the inner cavity first portion 132a (i.e., the end that includes the seating surface 114) and the ring member 400, the seal member distal portion 320 is maintained in mechanical and sealing engagement with the opposing seating surface within the inner cavity first portion 132a. Such mechanical engagement also is established such that the seal member distal portion 320 is essentially secured to the proximal housing 100a so as to resist axial forces imposed during operation of the seal member 300 as the in-line valve IV catheter is moved from and between the sealed and open configurations. Alternatively, the seal member distal portion 320 can be separately secured to the proximal housing 100a using any of a number of techniques known to those skilled in the art including the use of adhesives (e.g., epoxy), mechanical connections, welding (e.g., ultrasonic welding), brazing, chemical joining techniques and other techniques that are appropriate for the materials the housings are constructed from. Further, in this embodiment the ring member 400 can be dispensed with or provided so as to provide additional assurances that the seal member remains axially moveably disposed with the proximal housing 100a as herein described.

Figure 5:
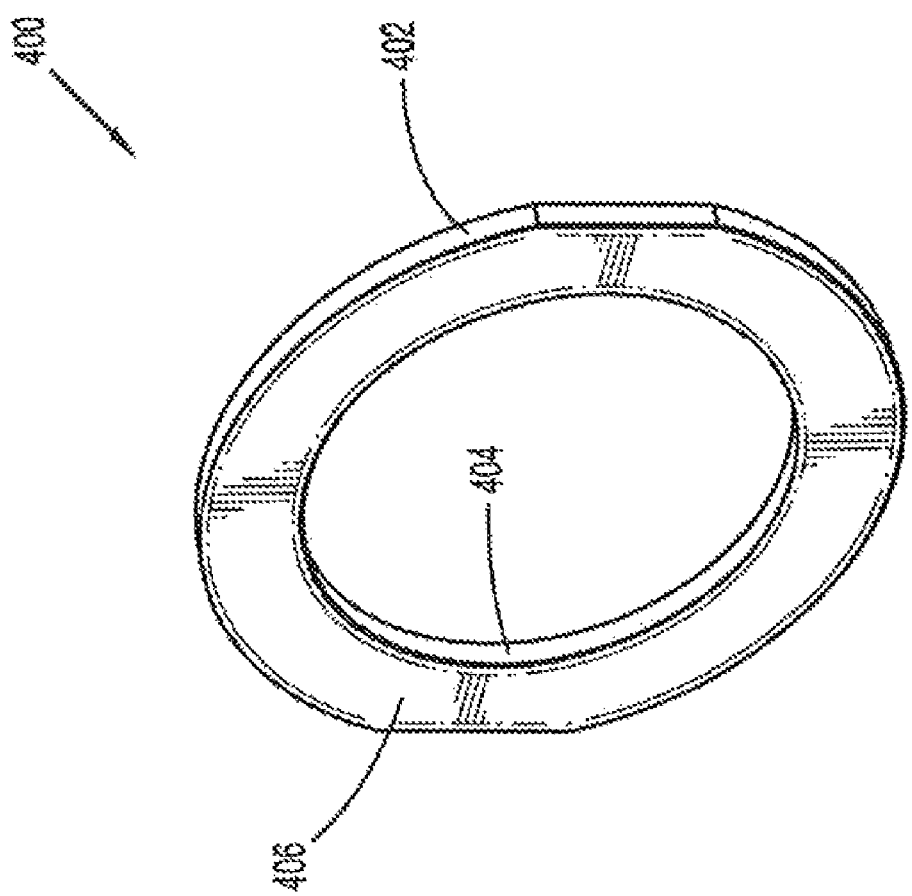
FIG. 5 is an axonometric view of a ring member of an in-line valve IV catheter

As illustrated in FIG. 5, the securing or locking ring member 400 is an annular plate like member. The diameter of the ring member outer circumference 402 (i.e., outer diameter) is generally set so a portion of the ring member is received in, and remains disposed within, the groove 140 (FIG. 3B) in the proximal housing 100a (i.e., outer diameter of ring member is larger than inner diameter of inner cavity on either side of the groove). The thickness of the ring member 400 also is set so the ring member has little to no axial movement within the groove 140 (FIG. 3B). Thus, when the ring member 400 is inserted into the groove 140, the ring member is maintained within the desired fixed relationship with respect to the seating surface 114. Stated another way, a snap-fit is established between the ring member 400 and the groove 140. Other ring member embodiments are described hereinafter.

Referring also to FIG. 2B, the diameter of the inner circumference 404 of the ring member 400 (i.e., inner diameter) is set so the ring member extends inwardly of the seal member distal portion 320 such that the seal member distal portion does not become disengaged from the ring member during use. Also, the diameter of the inner circumference 404 and the thickness of the ring member 400 is set so that the ring member has sufficient axial stiffness so the seal member 300 remains compressed and mechanically retained between the proximal end of the inner cavity first portion 132a and the ring member and also so the seal member sealing portion 330 remains sealingly engaged with the seating surface 114 (i.e., in the valve closed condition). In more particular embodiments, the inner diameter is set so the provided cross-sectional area is appropriate to establish desired fluid flow conditions (e.g., desired pressure loss and flow volume). In further embodiments, the inner diameter is set so that the ring member 400 has sufficient flexibility to allow the ring member to be manipulated within the inner cavity 130 and inserted into the groove 140.

While an inner circumference 404 of constant radius is illustrated, the inner circumference of the ring member 400 can be configured and arranged so as to form any cross-section that satisfies the foregoing described structural and flow considerations. For example, the inner circumference 404 can be hexagonal in cross-section or it can be made from one or more of through-apertures through the plate-like member making up the ring member 400. Such through-apertures can be arranged so that they overlap with each other so as to form a single-through aperture or arranged to form plurality of separate through apertures.

In a further embodiment, the ring member 400 includes a radial slit that extends between the outer and inner diameters thereof so the ring member is what is sometimes referred to as a split ring. In such a ease, the ring member material is selected so the ring member can be compressed circumferentially (i.e., Make the ring member outer diameter smaller) to facilitate insertion into the groove and so the ring member can return back to the desired outer diameter after insertion is completed.

It should be recognized that the foregoing described ring members are illustrative of a few examples of a mechanism for securing the seal member 300 to the proximal housing 100a. Thus, it is within the scope of the present invention to utilize any other technique known to those skilled in the at by which the seal member 300 can be secured to the proximal housing 100a and so as to be capable of carrying out the functions described herein for the seal member 300.

In yet further embodiments, following insertion of any of the herein described ring members into the groove 140, the ring member 400 is further secured to the proximal housing 100a using any of a number of techniques known to those skilled in the art as herein described. Such other techniques include, but are not limited to mechanical securing techniques such as adhesives or ultrasonic or vibration welding.

Referring to FIGS. 2B and 4A-4B, each window 340 in the seal member 300 is arranged so it extends between an exterior surface 304 of the seal member 300 and the inner seal member cavity 302 thereof, whereby fluid can flow in one direction through each of the windows into the inner cavity 302 (such as when fluid is being injected into the patient) or can flow in the opposite or another direction through the inner cavity 302 and out through the one or more windows 340 (such as when fluid is being extracted from the patient such as for sampling purposes). The number, shape and size of windows 340 is set so that the resultant cross-sectional area is appropriate to establish the desired fluid flow conditions (e.g., desired pressure loss and flow volume).

The number, location, shape and size of the windows 340 in the seal member also can be used to control the axial stiffness and stability of the seal member 300. The window placement controls the axial displacement force that would be applied to the proximal end 310 of the seal member 300 to cause the proximal end 310 to be moved axially to disengage the sealing portion 330 from the seating surface. The window placement also controls the restoring force that the seal member 300 would be capable of generating to restore the seal member to sealing engagement with the seating surface 114 after the axial displacement force is removed.

Figure 4D:
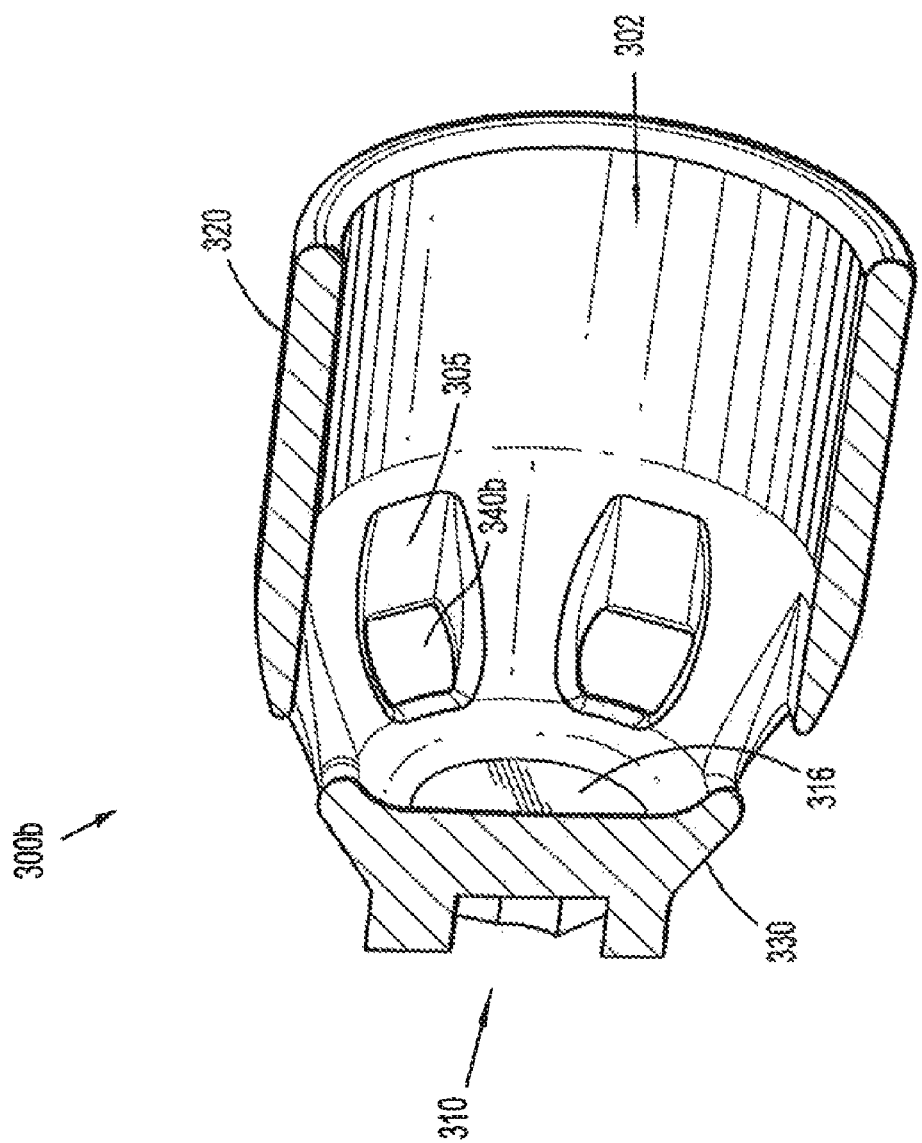

The proximal end 310 of the seal member 300 includes one or more raised sections 312 arranged about a centrally positioned chamber 313 and one or more passages or channels 314 between each of the one or more raised sections and which are fluidly coupled with the central chamber 313. The proximal end 310 also includes a septum 316 (FIG. 4D). The raised sections 312 and the channels 314 cooperate so that when the sealing portion 330 of the seal member 300 is displaced from the proximal housing seating surface 114, one or more flow paths are established between the centrally positioned chamber 313 and the sealing portion 330. Thus, when the sealing portion 330 is displaced from the seating surface 114 of the proximal housing 100a corresponding to an valve open condition, fluid can flow from/to the coupling end 110 of the proximal housing 100a, through the centrally positioned chamber 313 and the channels 314, about the seal member 300 and through a section of the inner cavity first portion 132a that is proximal to the seating surface 114 and the seal member windows 340, through the seal member windows 340, through the seal member inner cavity 302, through a portion of the distal housing inner cavity 230 and to/from the open end 252 of the tubular member 250.

Prior to use as an IV catheter, and as illustrated in FIG. 2A, a stylet/sharp/cannula 20 is disposed to pass through the centrally positioned chamber 313, through the septum 316 and through the seal member inner cavity 302. As also shown in FIG. 2A, the stylet/sharp/cannula 20 also passes through the second portion 132b of the proximal housing 100, the centrally located opening or through aperture in the ring member 400 (FIG. 5), through the inner cavity 230 of the distal housing 200 and out through the tubular member 250. The septum 316 and the proximal end 310 are made of a resilient material(s) that will re-seal themselves after the stylet/sharp/cannula 20 is withdrawn through the septum. It is contemplated that the sharp end of the stylet/sharp/cannula 20 can be used to form the opening in the septum 316 through which it would pass or another device or instrumentality can be used to form the opening initially in the septum 316 and thereafter the stylet/sharp/cannula 20 would be inserted through this initially formed opening by the opposite end or the sharp end 22 of the cannula 20.

Figure 8A:
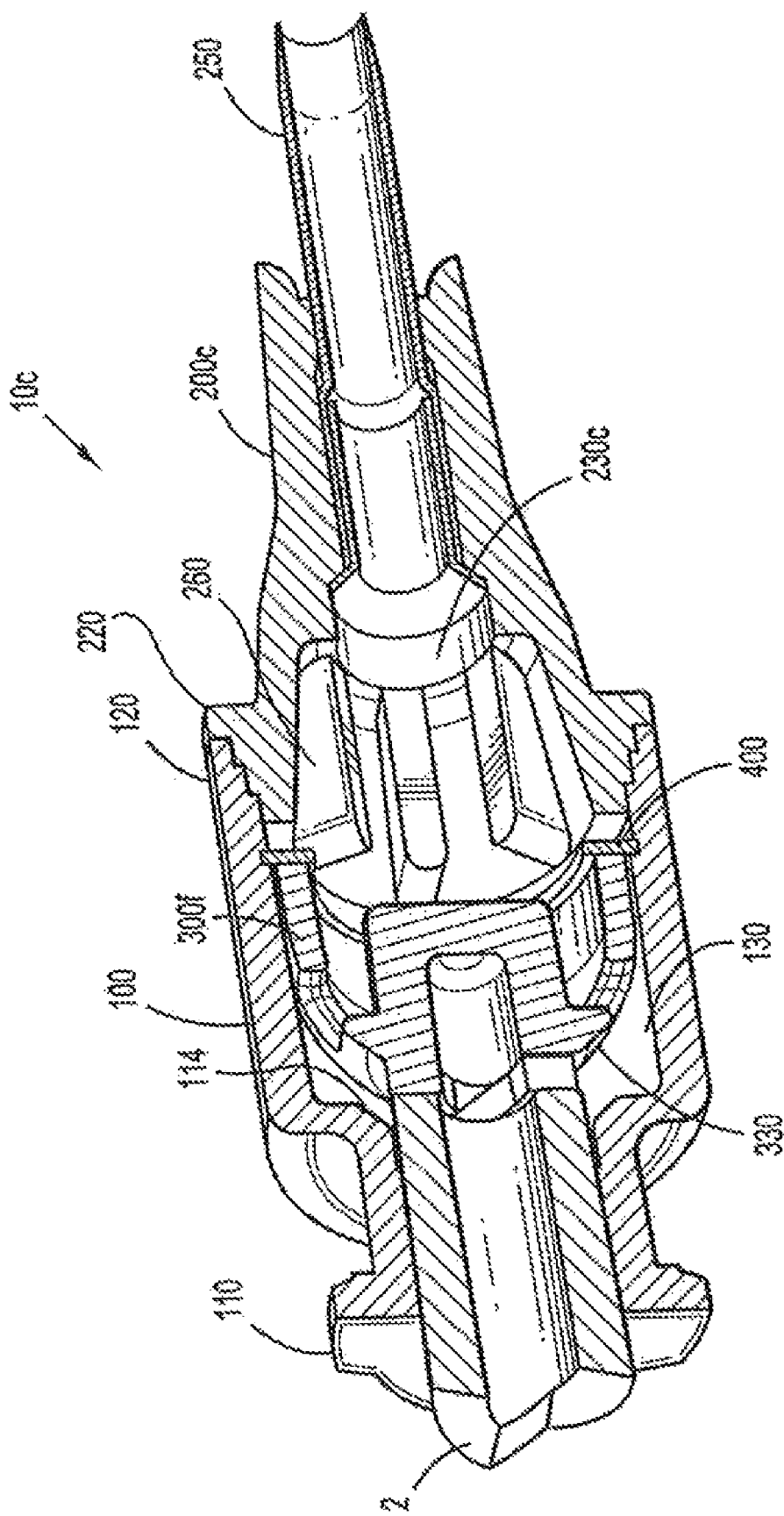
FIG. 8A is a cross-sectional isometric view of an embodiment of the in-line valve IV catheter of FIG. 7 having a distal housing with a different internal cavity structure (e.g., fins) as well as illustrating displacement of a sealing portion of the seal member responsive to the insertion of a nose of a luer device.

As shown in more clearly in FIG. 2B, the proximal end 310 of the seal member 300 extends into the second portion 132b of the inner cavity 130 of the proximal housing 100a when the sealing portion 330 of the seal member 300 is in sealing engagement with the seating surface 114 which corresponds to the valve closed condition. In use, when a portion of a syringe or other device (such as shown in FIG. 8A) is inserted into the opening in the coupling end 110 of the proximal housing 100a, the syringe or other device portion contacts and pushes against the proximal end 310 of the seal member 300. More specifically the syringe or other device portion contacts and pushes against the raised sections 312 of the proximal end 310. Such contacting/pushing thereby causes a force (e.g., an axial force) to be applied to the seal member proximal end 310 to thereby axially displace or move the sealing portion 330 from the seating surface 114 as illustrated for example in FIGS. 8A and 11B,C. As also indicated herein, such syringe or other device would be secured (i.e., removably secured) to the coupling end 110 of the proximal housing 100a using any of a number of techniques known to those skilled in the art (e.g., a luer connection).

As indicated above, such displacing opens up the valve embodied in the in-line valve IV catheter assembly 10a and also creates a flow path through the in-line valve IV catheter assembly. When the valve is thus opened, a fluid pathway is thereby established between the syringe or other device and the open end 252 of the tubular member 250. In this way, fluid can flow in either direction through the in-line valve IV catheter assembly as described in more detail herein so that fluid can be introduced into the blood vessel in which the tubular member 252 is inserted into or so a fluid sample can be extracted from such a blood vessel.

When the syringe or other device is decoupled from the coupling end 110 and removed from the second portion 132b, the force that was acting on the proximal end 310 of the seal member 300 is removed. When such force is removed, the resiliency of the seal member 300 causes the seal member to move axially towards the seating surface 114 (i.e., away from the ring member 400) until the sealing portion 330 thereof sealingly engages the seating surface 114 of the proximal housing 100a. In this way, the valve formed by the cooperation of the proximal housing 100a, the seal member 300 and the ring member 400 is again closed preventing flow of fluid through the in-line valve IV catheter assembly 10a. The foregoing described operation of coupling a syringe or other device to the proximal housing 100 can be repeated as and when needed/desired by medical personnel.

As described herein in an alternative embodiment, the proximal housing 100a is configured without a groove 140 and instead, the inner cavity first portion 132a is formed so as to have at least two sections, each section having different inner diameters so as to form a shoulder 142 (FIG. 3B). The inner diameter of the first section, as describe above, is set so as to have a close fit with the distal portion 320 of the seal member 300. The inner diameter of the other section is established so at least the portion thereof proximal to the first section corresponds to the depth of the groove 140. The intersection of these two different inner diameters, namely the shoulder 142, is set so as to be at the location corresponding to the location of a front edge of a groove 140. When assembling the catheter assembly using such a proximal housing, the ring member 400 would be manipulated until it abuts the shoulder 142 formed by the intersection and then the ring member would be secured in place using any of a number of techniques known in the art (e.g., adhesives, vibration welding).

In a further alternative embodiment, the ring member 400 and the groove 140 are replaced by a raised region, rib or stop (not shown) that extends about the circumference of the inner cavity at about the same location as the groove 140 and upwardly from the inner surface towards the longitudinal axis of the proximal housing 100a. The seal member 300 would be inserted through the central opening formed by the raised region and manipulated so that the seal member was sealed and mechanically retained between the raised region and the seating surface 114.

In yet a further alternative embodiment, the proximal housing 100a is configured without a groove 140 and instead, the inner cavity first portion 132a is formed so the inner diameter thereof is set so that when the seal member 300 is compressibly and mechanically retained within the proximal housing 100a, the seal member distal portion 320 is maintained in mechanical and sealing engagement with the opposing surface of the inner cavity first portion 132a (i.e., there is an interference fit between the seal member distal portion 320 and the opposing surface of the inner cavity first portion 132a). This mechanical engagement is such as to resist axial movement of the seal member distal portion 320 with respect to the proximal housing 100a when the seal member is either in the valve open configuration or the valve closed configuration.

Referring now to FIGS. 4C-4G, there are shown some illustrative embodiments of seal members 300b-e for use with any of the in-line valve IV catheter assemblies 10a-c described herein. Reference shall be made to the foregoing discussion regarding FIGS. 1-3 and 4A,B for details or characteristics regarding the seal member not otherwise described or detailed below.

Referring now to FIGS. 4C, D there is shown another embodiment of a seal member 300b in perspective and cross-sectional view, respectively. This embodiment differs from that illustrated in FIGS. 4A, B in that each of the windows 340b is formed in the seal member 300b so that a region 305 (FIG. 4D) about the actual opening is recessed in an axial direction between the opening and the distal end of the seal member 300b.

Referring now to FIG. 4E there is shown another embodiment of a seal member 300c. This embodiment as with the seal member 300b illustrated in FIGS. 4C, D includes windows 340b that are formed in the seal member 300c so that a region 305 about the actual opening is recessed in an axial direction between the opening and the distal end of the seal member 300c. This illustrated embodiment differs from that illustrated in FIGS. 4C, D in that the distal portion 320c is shortened axially as compared to the distal portion 320 illustrated in FIGS. 4C, D.

Figure 4F:
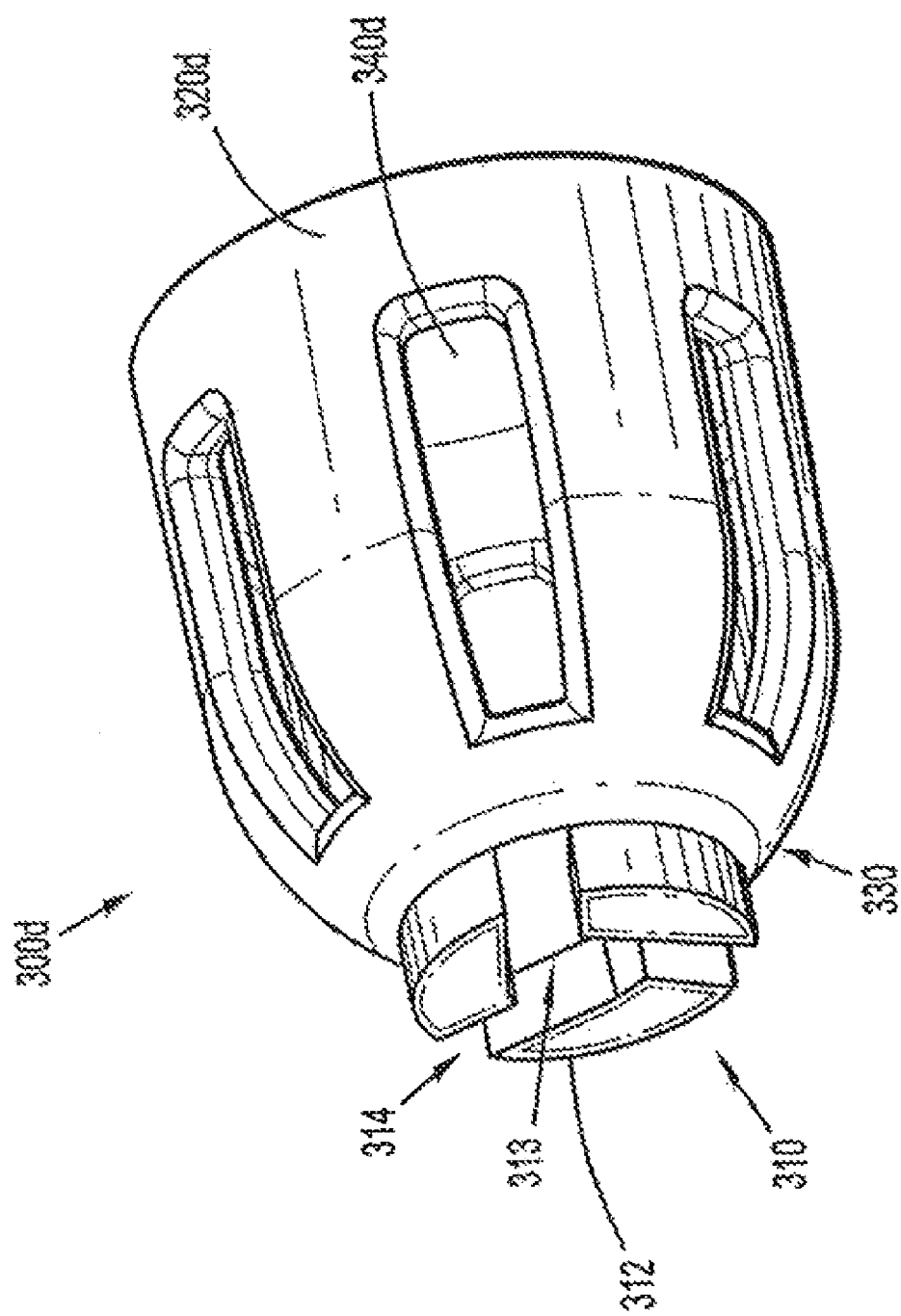
Figure 4G:
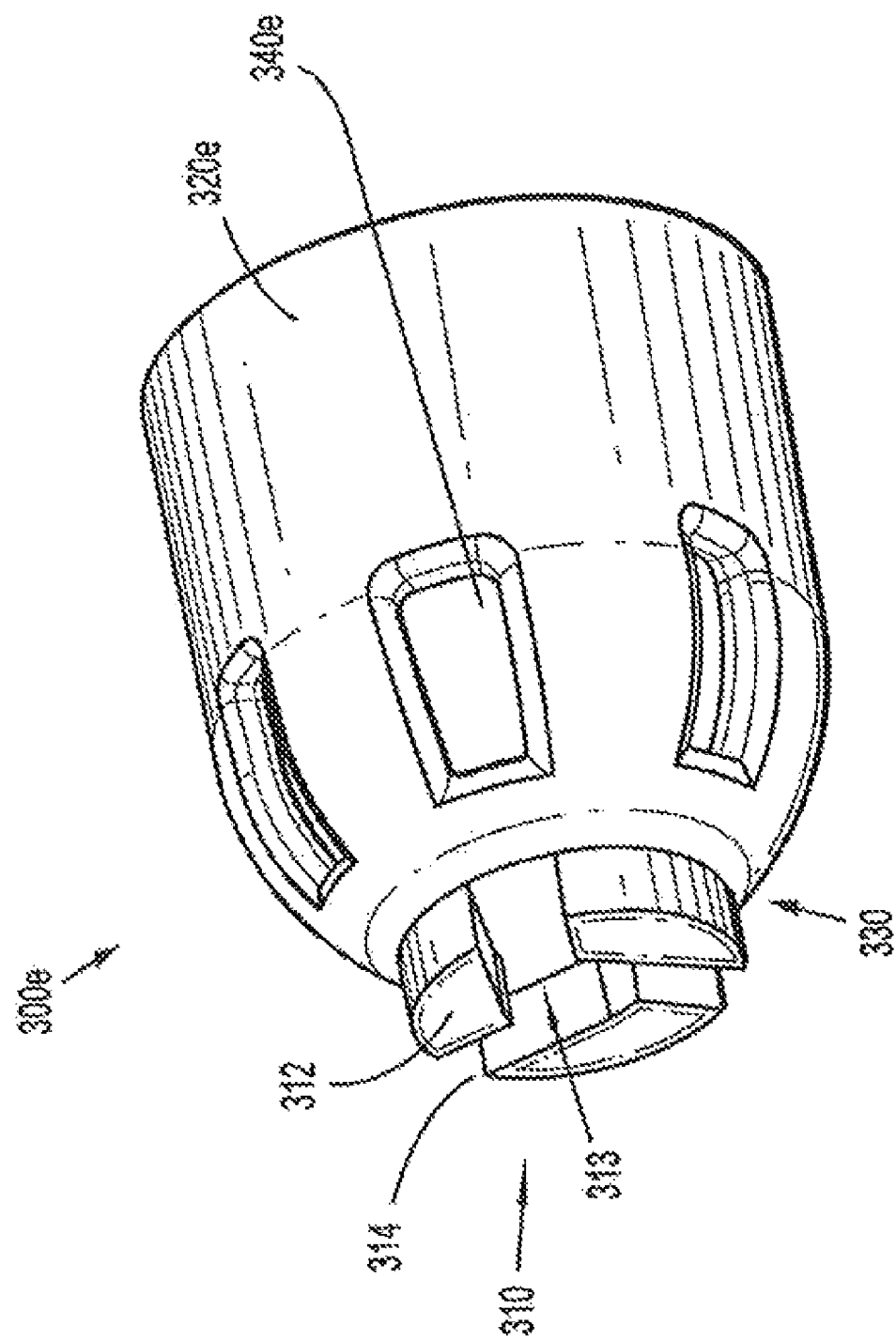

Referring now to FIGS. 4F, G there are illustrated further seal member embodiments. These seal members 300d, e include one or more of windows 340d,e (e.g., a plurality) that are generally rectangular in cross-section and extend lengthwise along the long axis of the seal member 300d. While increasing flow area, these windows 340d also are illustrative of the use of windows 340d to control the axial flexibility or stiffness of the portion of the seal member that applies the force to put the sealing portion 330 in sealing engagement with the seating surface 114 of the proximal housing and also which resists the application of the external force by a syringe or other device inserted into the coupling end 110 of the proximal housing to displace the sealing portion 330 from the seating surface 114.

Figure 6A:
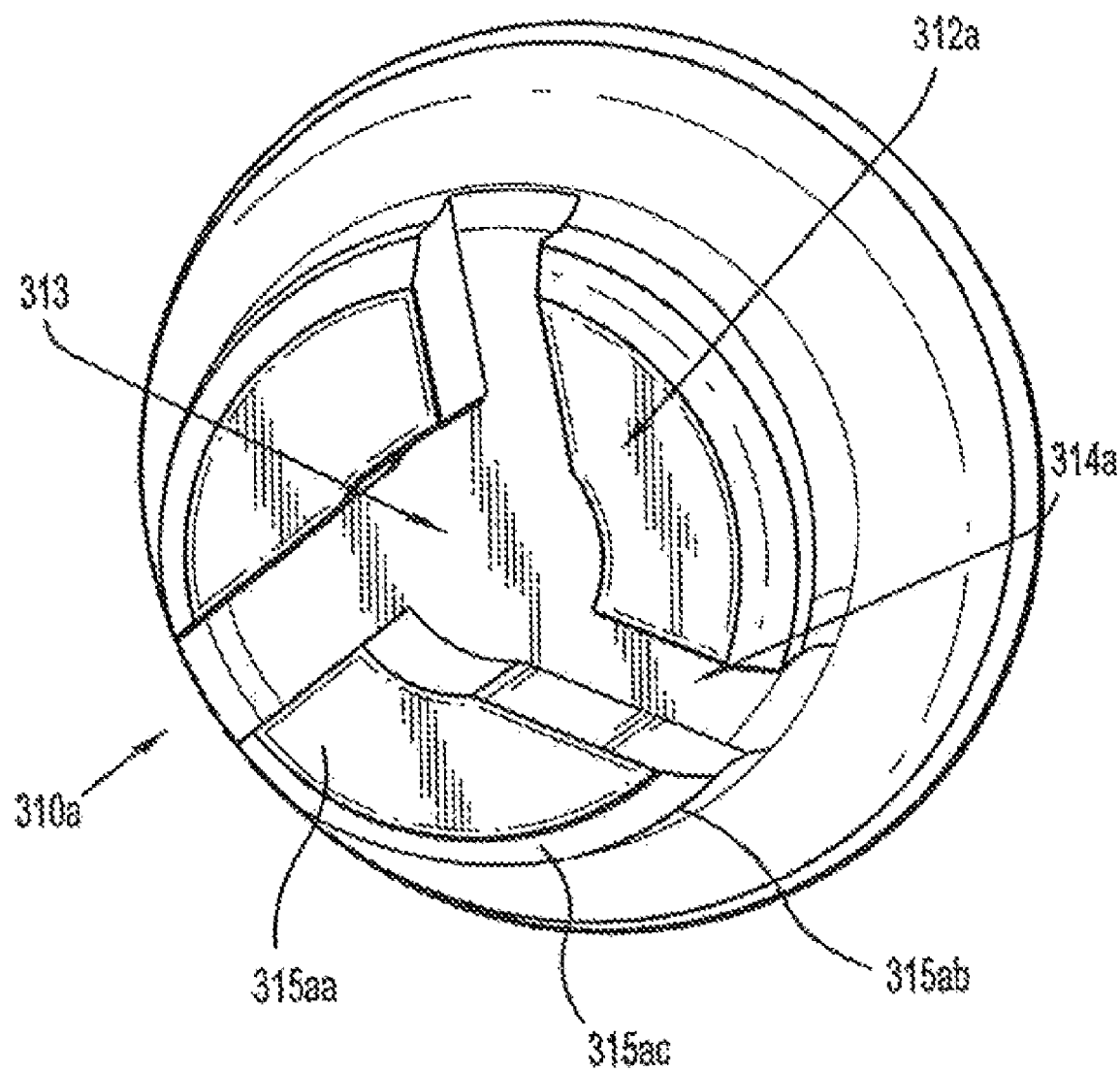
FIGS. 6A-C are end views illustrating some embodiments of the proximal end of a seal member.
Figure 6B:
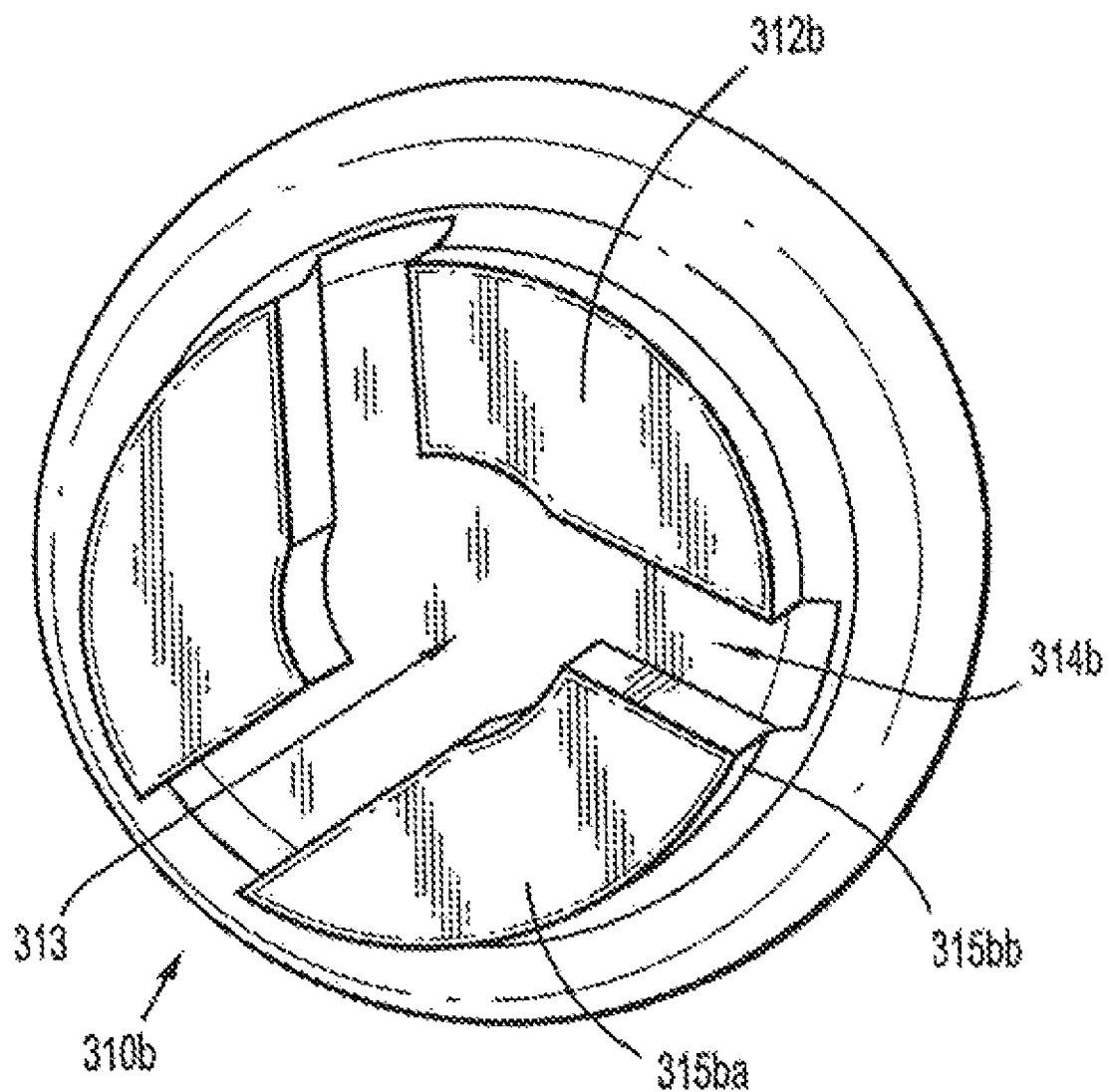
Figure 6C:
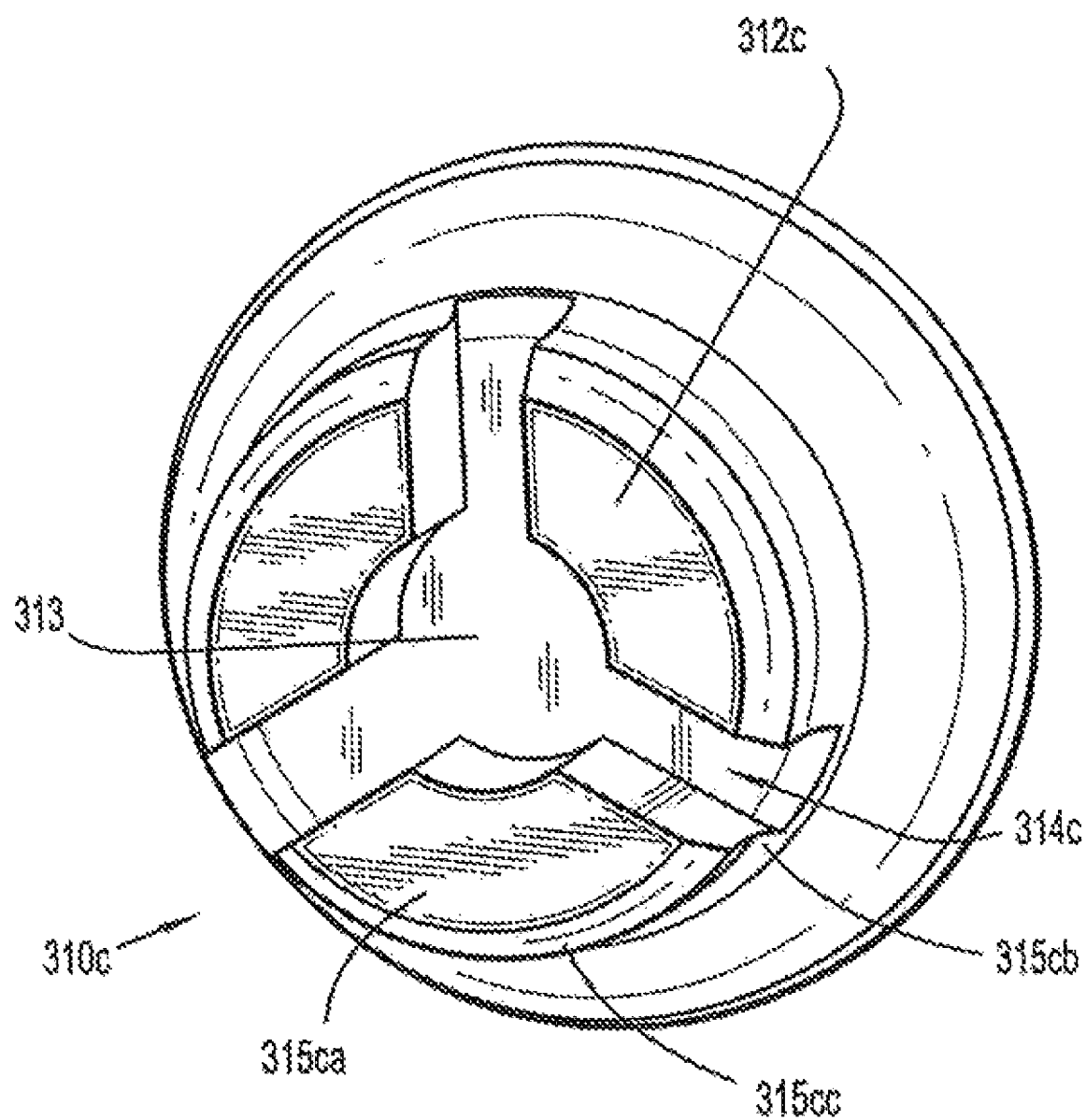

Referring now to FIGS. 6A-C there are shown illustrative orientations of arranging the channels 314a-c and raised sections 312a-c of the proximal ends 310a-c for any of the seal members 300-300e described herein and for use in any of the in-line valve IV catheters described herein. In use, the specific method used to couple the syringe or other device to the coupling end 110 of the proximal housing may involve applying non-axial forces on the raised sections, which forces might tend to distort the channel shape which could result in the partial or complete closure of one or more channels.

For example, a conventional luer connection typically involves a clockwise twisting or rotational motion to secure the male and female connectors together. Thus, when the nose portion of the luer is in contact with the raised sections a rotational or twisting force would be applied to the raised sections.

Thus, and as shown in FIGS. 6A-B the orientation of the raised sections 312a,b and channels 314a,b can be altered so that the structure associated with a given orientation offers better resistance against complete closure of the flow path. For example, the orientation illustrated in FIG. 6B is believed to yield a structure that would be better resistant to the clockwise twisting motion that a male luer uses to engage the luer end connection detail ("crown") of the coupling end 110 which could lead to partial closure of the one or more channels. Correspondingly, the channel and raised section 312a, 314a orientation of FIG. 6A would be considered for use to resist a counterclockwise twisting motion.

As also illustrated in FIG. 6A, the raised sections 312a can be configured so that a portion 315ac of the upper surface 315aa of a raised section is sloped towards the rising circumferential outer surface 315ab of the raised section (e.g., chamfered). Alternatively, the proximal end 31b also can be configured as shown in FIG. 6B so the upper surface 315ba of the raised section 312b is arranged so as to be substantially at right angles (i.e., not a chamfered/sloping surface) with respect to the rising circumferential outer surface 315bb of the raised section. The alternative embodiment maximizes the contact surface between the crown of the proximal end 310 formed by the raised sections 312b and the opposing surface of the device portion being inserted into the proximal housing coupling end 110. The alternative embodiment also is advantageous when the device portion being inserted is in the form of a tubular member. The omission of a sloping surface in the alternative embodiment lessens the possibility that a twisting motion by the device portion could cause the raised sections to move inside the tubular member and thus effectively block the flow path.

As illustrated in FIG. 6C, the raised sections 312c and channels 314c of the proximal end 310c also can be oriented so that the channels 314c extend radially outwardly from the centrally positioned chamber 313. The illustrated proximal end is similar to that illustrated in FIG. 6A including having the raised section 312c configured so that a portion 315cc of the upper surface 315ca of a raised section is sloped towards the rising circumferential outer surface 315cb of the raised section (e.g., chamfered).

Figure 7:
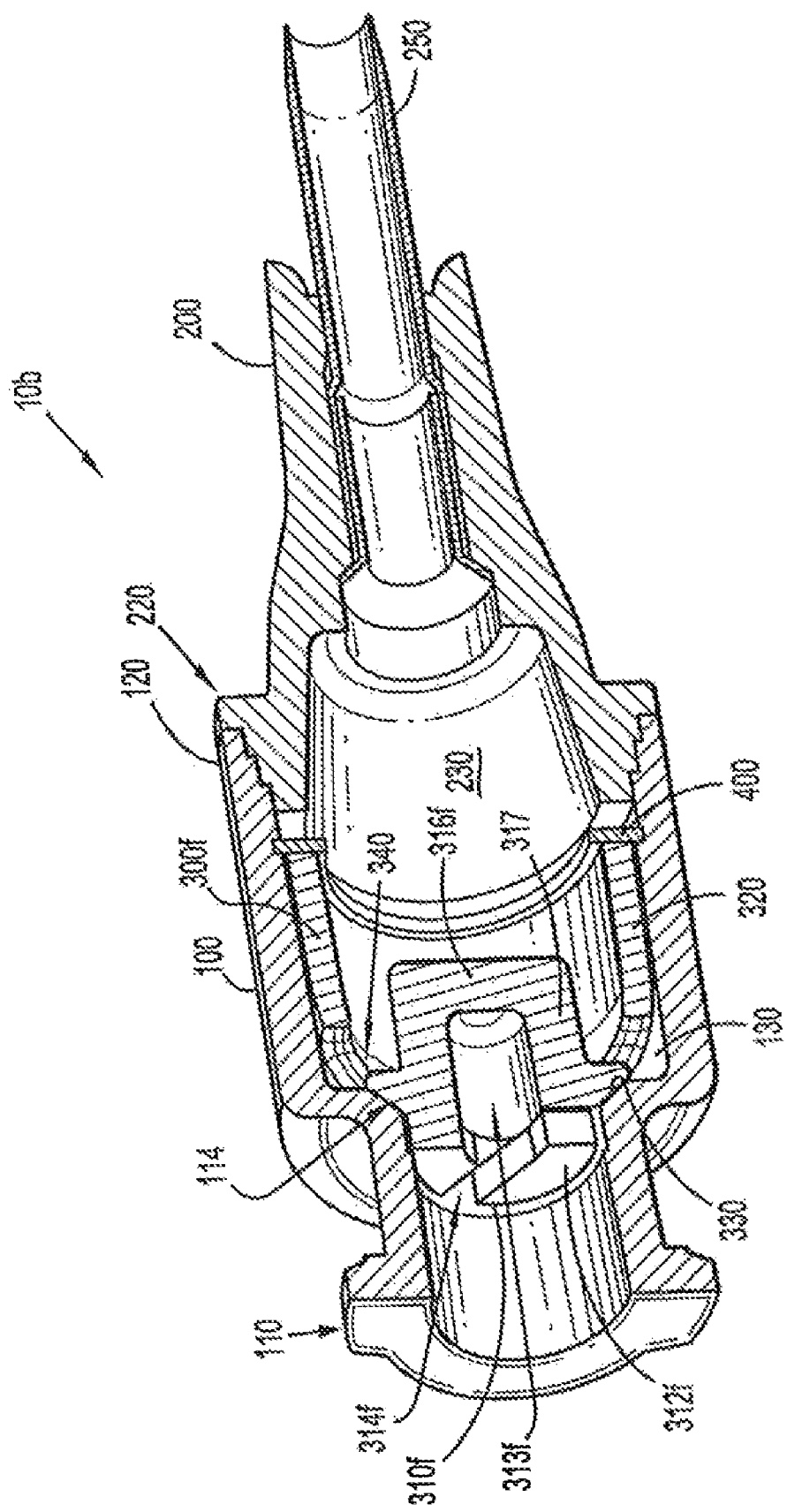
FIG. 7 is a cross-sectional isometric view of another aspect of an in-line valve IV catheter of the present invention having a seal member with a remote septum and without the object/needle/cannula.

Referring now to FIG. 7, there is shown a cross-sectional isometric view of an in-line valve IV catheter assembly 10b including a seal member 300f having a septum 316f that is remote from the sealing portion 330 thereof. The object being inserted through the septum 316f such as an insertion stylet/sharp/cannula 20 is not shown in this view for clarity; however, such an insertion stylet/sharp/cannula 20 would be disposed in the in-line valve IV catheter assembly 10b as shown in FIG. 2A so it passes through the remote septum 316f. Reference shall be made to the foregoing discussion regarding FIGS. 1-6 for details or characteristics regarding the proximal and distal housings 100, 200, the ring member 400 and the seal member 300 not otherwise described or detailed below.

The proximal end 310f of this seal member 300f includes one or more raised sections 312f, each being arranged about a central chamber 313f and one or more channels 314f between each of the one or more raised sections 312f and which are fluidly coupled with the central chamber 313f. The central chamber 313f also includes a side wall(s) 317 that extend axially from the proximal end to the distally located septum 316f and about a long axis. Although the side wall(s) 317 is arranged so as to form a cylindrical structure, the side wall(s) 317 can be arranged so as to form any of a number of three-dimensional structures (e.g., hexagonal).

Figure 8B:
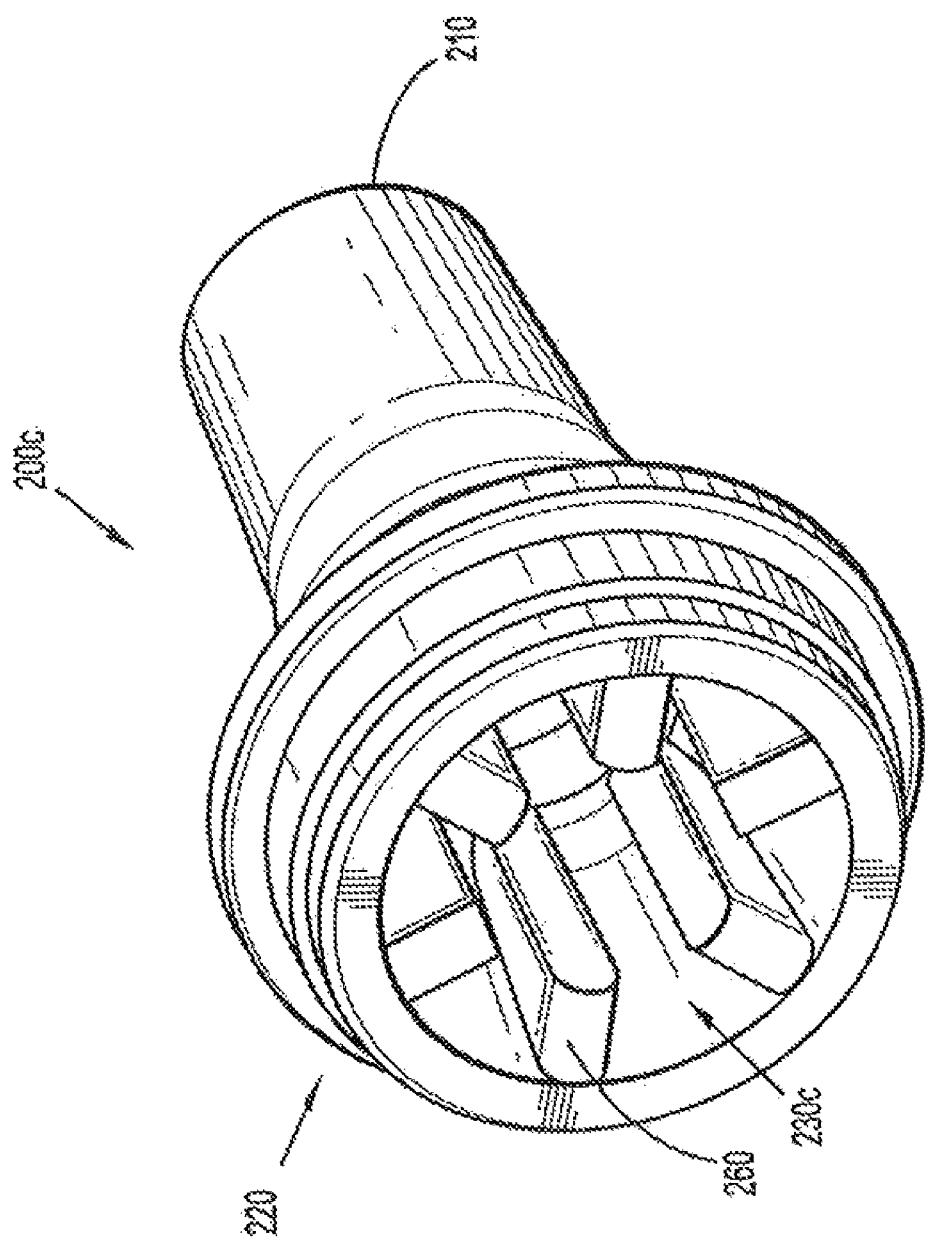
FIGS. 8B, C are an axonometric and cross-sectional isometric view respectively of the distal housing of the in-line valve IV catheter of FIG. 8A.

Referring now to FIGS. 8A, there is shown a cross-sectional isometric view of an embodiment of the in-line valve IV catheter 10c including a distal housing 200c with a different internal cavity structure as well as illustrating displacement of the sealing portion 330 of the seal member 300f from the seating surface 114 of the proximal housing 100 responsive to the insertion of a syringe member 2. There also are shown in FIGS. 8B,C isometric and cross-sectional isometric views respectively of the distal housing 200c of the in-line valve IV catheter 10c of FIG. 8A.

Reference shall be made to the foregoing discussion regarding FIGS. 1-6 for details or characteristics regarding the proximal and distal housings 100, 200, the ring member 400 and the seal member 300f not otherwise described or detailed below. Reference also shall be made to the foregoing discussion regarding FIG. 7 for details or characteristics regarding the seal member 300f not otherwise described or detailed below.

The distal housing 200c includes one or more, more particularly a plurality, yet more particularly three or more, more specifically four or more fins 260 that extend radially inwardly into the inner cavity 230c of the distal housing 200c. The radial fins 260 are spaced from each other so as to form an open area through which the stylet/sharp/cannula 20 passes when it is disposed within the IV catheter 10c. The fins 260 also are arranged so that they do not contact the ring member 400 or the seal member 300f when the seal member 300f is in sealing engagement with the proximal housing seating surface 114. In addition the fins 260 are arranged so as to be spaced from each other to create an open area sufficient for the desired flow of fluid through the IV catheter 10c.

The fins 260 also are arranged so as to form a stop like structure within the distal housing 200c. Specifically, the fins 260 are arranged so that each of fins 260 presents a radially extending surface, which is located a predetermined distance from the ring member 400. The predetermined distance is set so as to prevent the seal member 300f from inverting or folding in on itself responsive to a severe momentary pressure spike or surge of a fluid being injected and being disposed within the inner cavity 230c of the distal housing 200c. Thus, when pressure is reversed within the in-line valve IV catheter, the seal member 300f will move axially in a direction such that the sealing portion 330 again sealingly engages the seating surface 114 of the proximal housing 100 thereby causing the in-line valve IV catheter 10c to attain a closed condition. It should be noted that except in the above-described abnormal operating condition when the seal member 300f or valve is in the open condition, the fins 260 never contact the seal member 300f. Also the fins 260 are not used to sealingly engage the sealing portion 330 of the sealing member 330c with the seating surface 114.

Although radially extending fins 260 are described, it should be recognized that the present invention is not so limited and that a distal housing 200 of the present invention can be configured so as to include extending fins or the like that extend generally inwardly from an inner surface of a portion of the inner chamber disposed within the distal portion. Such fins are arranged so as to create any of a number of structural arrangements know to those skilled in the art and appropriate for the intended use. In general, such a structural arrangement is arranged to form a physical barrier or stop to limit axial movement of a seal member to high pressure flow fluid conditions while maintaining adequate flow area for passage of fluid through the IV catheter in either distal or proximal directions. Such an arrangement also should allow the object (e.g., introducer needle, insertion needle/cannula or the like) to pass through the IV catheter. More particularly, the fins are arranged so they do not contact the seal member or the securing mechanism (e.g., the ring member) when the IV catheter is in the valve closed or sealed condition/position.

Figure 8D:
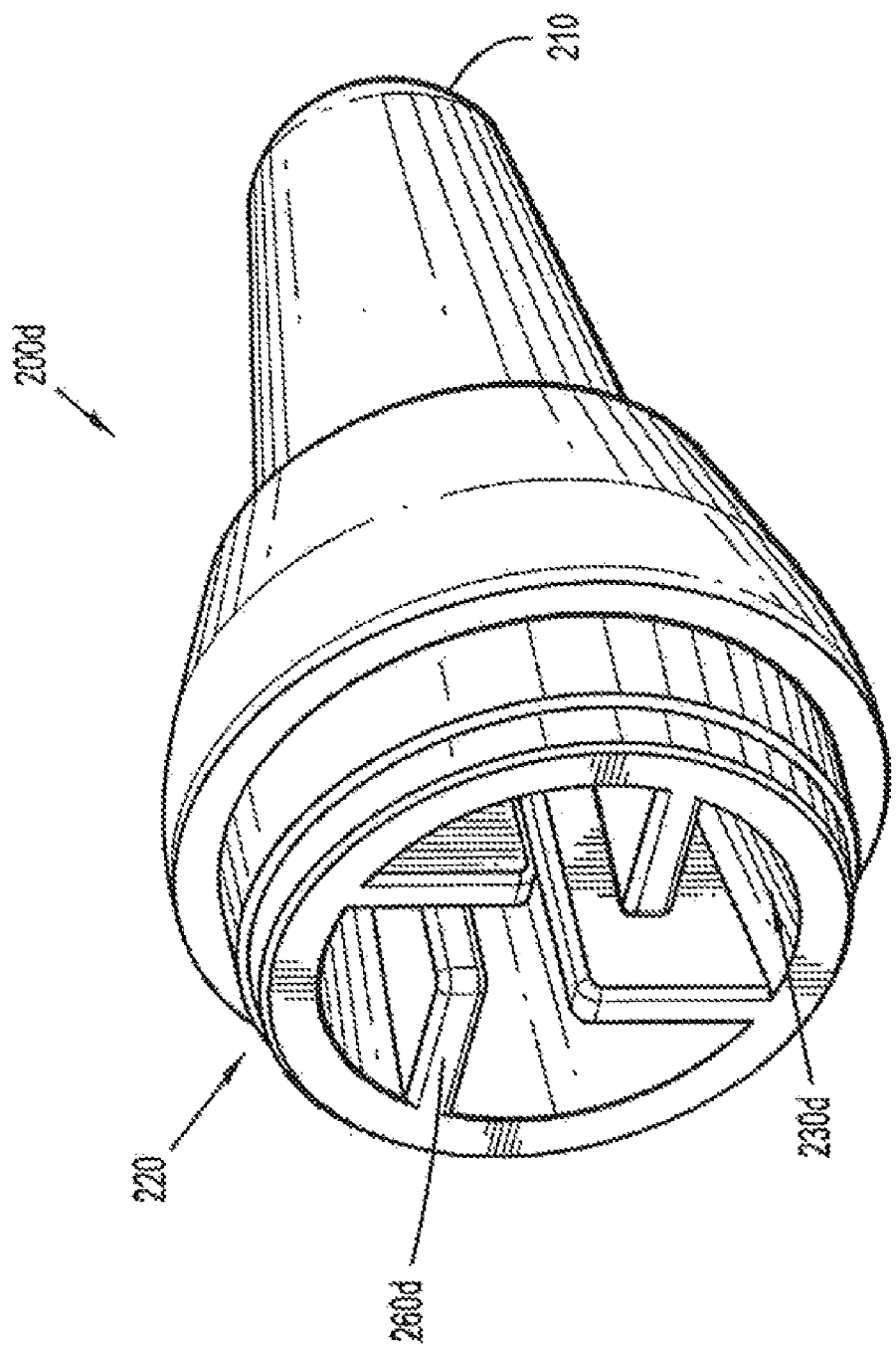
FIG. 8D is an axonometric view of a distal housing having another internal cavity structure (e.g., non-radial fins)

Referring now to FIG. 8D, there is shown one illustrative alternative embodiment in which the distal housing 200d includes one or more, more particularly a plurality, yet more particularly three or more, more specifically four or more non-radial fins 260d. In the illustrated embodiment, the plurality of axially extending fins 260d extend inwardly from the inner surface of the distal housing 200d in a non-radial fashion, where the fins are spaced from each other to provide a generally centrally located axially extending open region through which the introducer needle or the like can pass and to provide an open area for fluid flow.

Figure 8F:
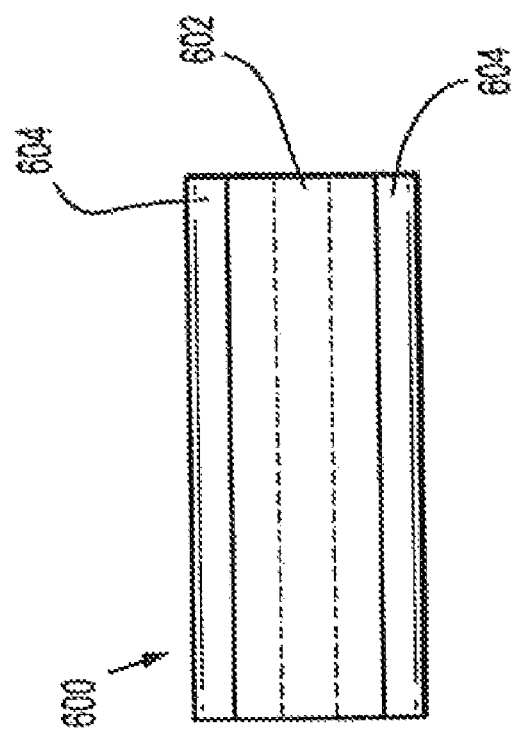
FIG. 8F is a side view of an intermediary member matable between and to the proximal and distal housings and including a stop structure.
Figure 8E:
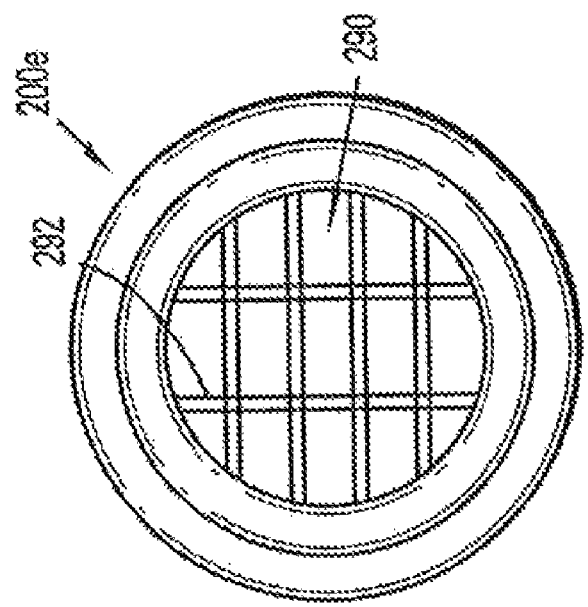
FIG. 8E is an end view of a distal housing having another internal cavity structure (e.g., grate structure)

In yet other exemplary embodiments, the distal housing 200e (FIG. 8E) includes a grate like structure 290 (e.g., a structure composed of members 292 that extend chord like across the inner surface of the distal housing and intersect. Such intersecting members 292 also are arranged so to form a stop structure that is opposite to the seal member septum and so as to provide a centrally located open region through which the introducer needle passes as well as providing an open flow area for the passage of fluid. It should be recognized that the structure illustrated is exemplary and the grate can be arranged in any of a number of fashions (e.g., members extending at angles with respect to each other). It also should be recognized that members can be arranged so they do not interact each other.

In yet another exemplary illustrative embodiment, the distal housing 200f (FIG. 10B) is configured so as to include one or more, more particularly a plurality, yet more particularly three or more, more specifically four or more radially extending fins 260f. The fins also are configured arranged so a portion 261 of the fins extends axially in a proximal direction into a portion of the proximal housing 100a. These portions 261 are configured so that they do not contact the ring member 400 or the seal member 300 when the seal member 300 is in the sealed configuration as herein described. These portions 261 of the fins 260f also are configured so the end portions thereof are a predetermined distance from the septum 316 when the seal is the sealed configuration. The axial length of these portions 261 is generally set to limit the axial travel for the septum 316 when the seal member proximal end 310 is exposed to a high pressure or high fluid flow condition as herein described.

In yet a further embodiment, an IV catheter device according to the present invention includes an intermediary member 600 (FIG. 8F) that includes the stop like structure 602 including any of the herein described structures (e.g., radial fins, non-radial fins, grate like structure). The intermediary member also includes mating ends 604 that are configured so the intermediary member is connected between and mated to the mating ends 120, 220 respectively of the proximal and distal housing 100a, 200 (FIG. 2B).

It also is within the scope of the present invention to adapt the ring member 400 of the present invention so it provides a stop like structure as herein described. For example, a grate structure 290 (FIG. 8E) could be formed so as to extend between the inner circumference 404 of the ring member 400 (FIG. 5).

Figure 9A:
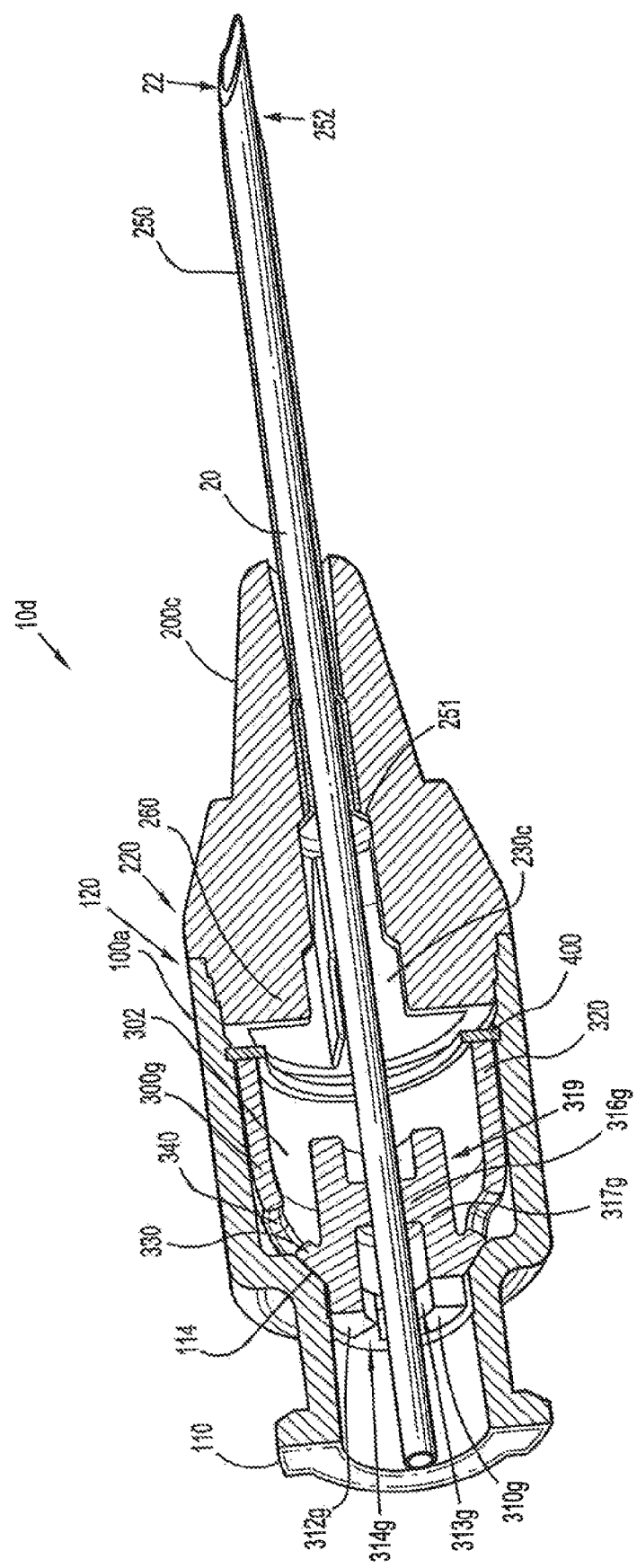
FIG. 9A is a cross-sectional isometric view of another aspect of an in-line valve IV catheter having a seal member with a remote septum that includes a collar portion with the object/needle/cannula inserted therethrough.
Figure 9B:
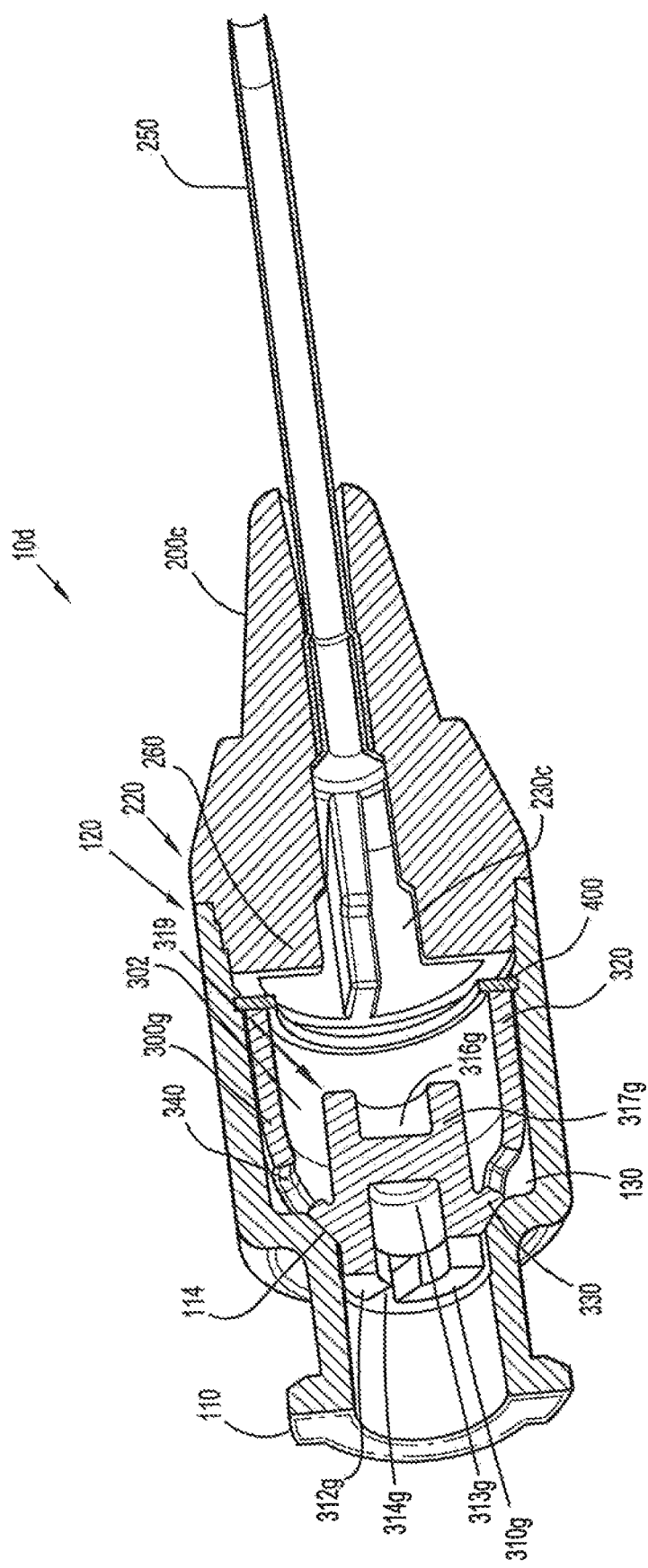
FIGS. 9B-D are various cross-sectional views of the in-line valve IV catheter of FIG. 9A with (FIG. 9C) and without (FIGS. 9B, D) the object/needle/cannula.
Figure 9C:
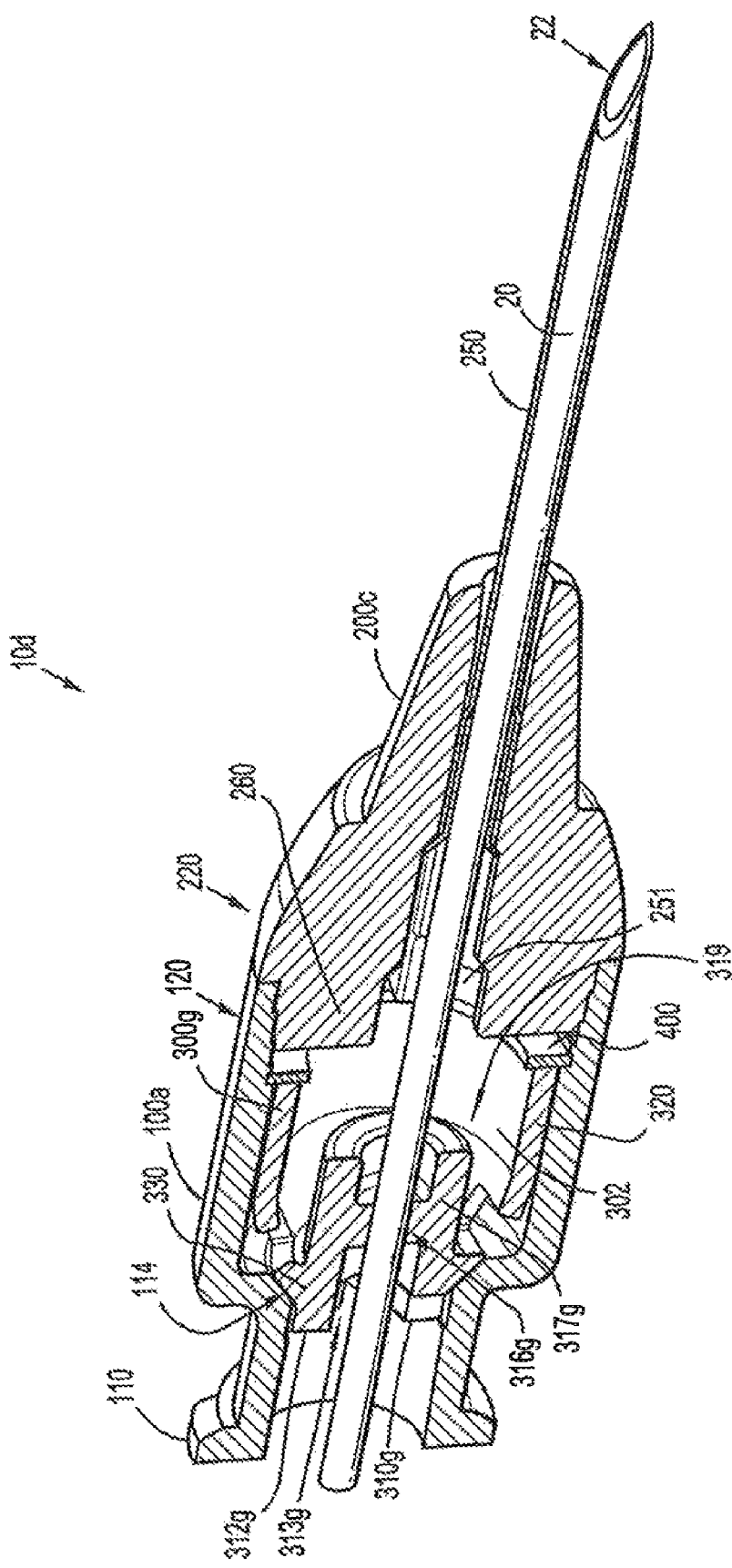
Figure 9D:
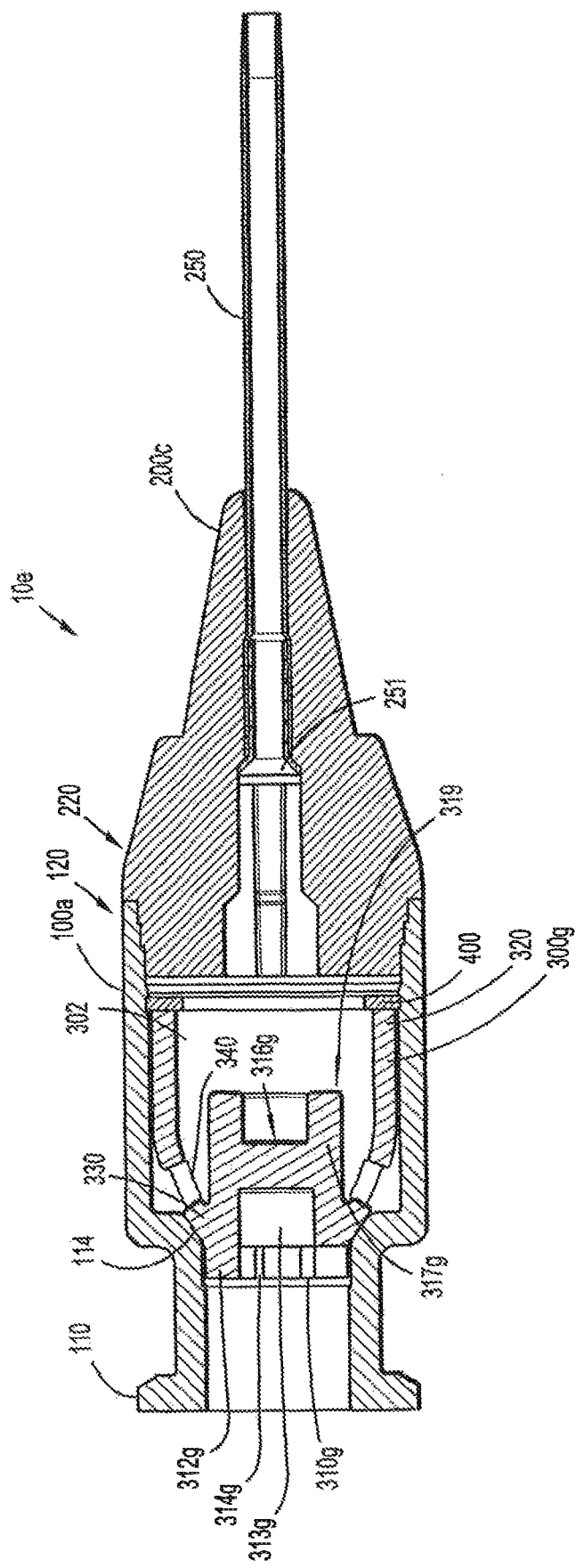

Referring now to FIGS. 9A-D, there are shown various cross-sectional views of another aspect of an in-line valve IV catheter 10d having a seal member 300g with a remote septum 316g and a collar portion 319 that extends outwardly from the remote septum. Such an in-line valve IV catheter 10d also is shown with an insertion stylet/sharp/cannula 20 that is inserted therethrough (FIGS. 9A, C) and without the insertion stylet/sharp/cannula inserted therethrough (FIGS. 9B, D). Reference shall be made to the foregoing discussion regarding FIGS. 1-8 for details or characteristics regarding the proximal housing 100a, the distal housing 200c, the ring member 400 and the seal member 300 not otherwise described or detailed below.

The proximal end 310g of this seal member 300g includes one or more raised sections 312g, each being arranged about a central chamber 313g and one or more channels 314g between each of the one or more raised sections and which are fluidly coupled with the central chamber 313g. The central chamber 313g also includes a side wall(s) 317g that extends axially from the proximal end and past the remote septum 316g and about a long axis. The side wall(s) 317g extends beyond the septum 316g so as to create the collar portion 319 that extends outwardly from and beneath the septum. Although the side wall(s) 317g is arranged so as to form a cylindrical structure, the side wall(s) 317g can be arranged so as to form any of a number of three-dimensional structures (e.g., hexagonal). As shown in FIG. 9A, the insertion stylet/sharp/cannula 20 is disposed in the in-line valve IV catheter assembly 10d as shown in FIG. 2a so it passes through the remote septum 316g and passes through the collar portion 319.

Without being bound to any particular theory or principle of science, the collar portion 319 enhances the ability of the septum 316g to self-close or self-seal itself after the insertion stylet/sharp/cannula 20 is removed from the septum. Also, the collar portion 319 enhances the ability of the septum 316g to limit or resist propagation of any tears that may originate in the septum. These advantageous effects are attributed to the presence of the collar portion 319 and the effect such a structure has on enhancing or increasing the radial stiffness of the septum 316g.

Figure 9E:
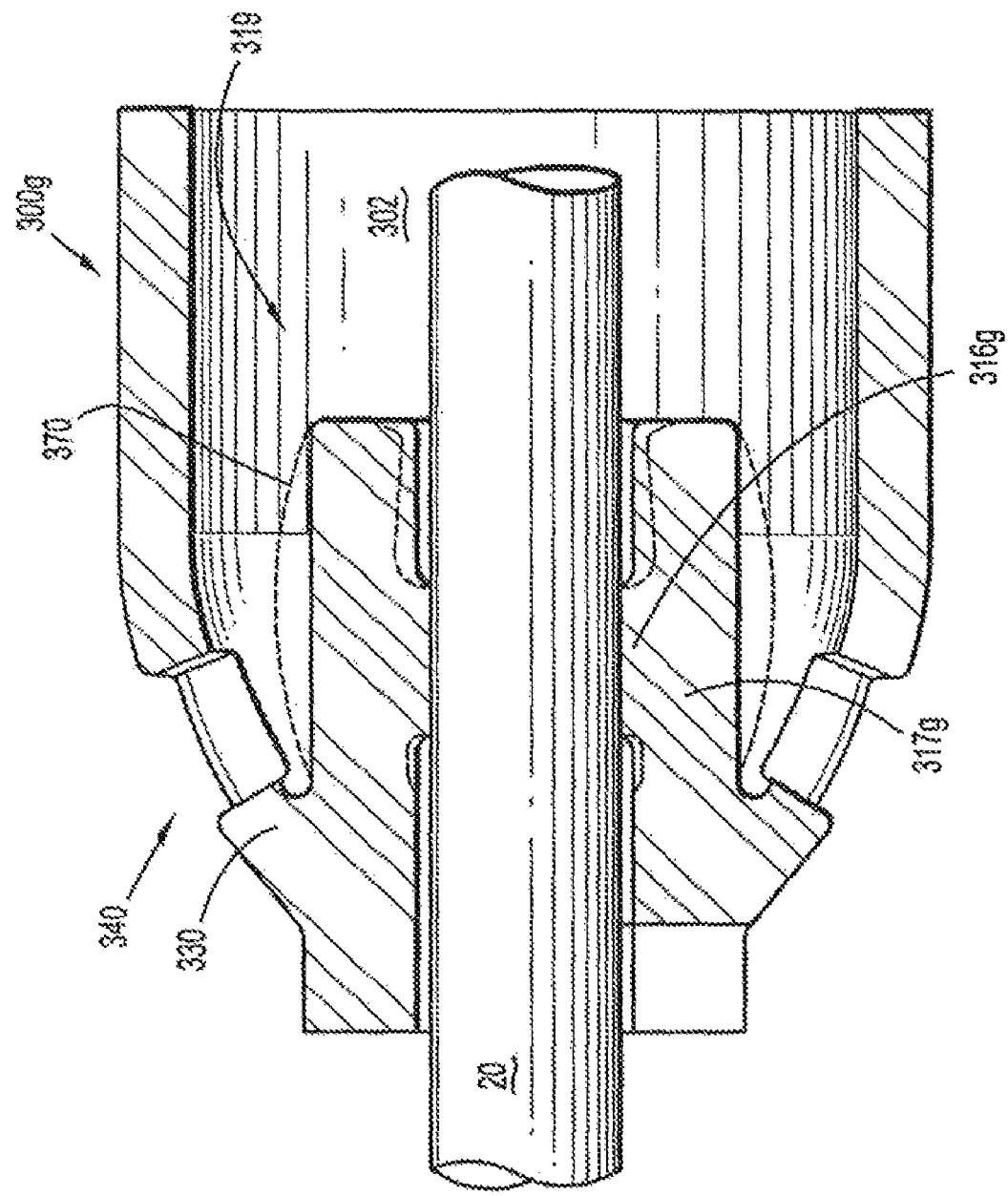
FIG. 9E is a cross-sectional view of the seal member with a remote septum that includes a collar portion illustrating the effect of insertion of an object/needle/cannula through the septum.

As shown in FIG. 9E, when the insertion stylet/sharp/cannula 20 is inserted through the septum 316g, the sidewalls 317g and the collar portion 319 are deformed from the normal position (shown as the solid lines) due to the presence of the insertion stylet/sharp/cannula 20. The deformation is illustrated by the broken lines 370. The amount of deformation is dependent upon the size or diameter of the insertion stylet/sharp/cannula 20.

As also illustrated in FIG. 9E, the location of the septum 316g remote from the sealing portion 330 of the seal member also has the beneficial effect that the deformation occurs within the seal member inner cavity 302. Consequently, the deformed portions do not contact the proximal housing 100a (FIG. 2B) and thus compressive forces are only being imposed by the collar 319, and not by the proximal housing 100a, as the insertion stylet/sharp/cannula is both being inserted through the septum 316g and when the insertion stylet/sharp/cannula is being withdrawn from the septum. In other words, the deformed portions of the collar 319 add a closure force to the remotely located septum 316g; however, if the deformed portions come into contact with a rigid housing such as the proximal housing 100a, the compressive forces can overly compress the septum. Consequently, the force being applied by the clinician during withdrawal of the insertion stylet/sharp/cannula 20 with such a remotely located septum 316g would be less than the force that would be required for withdrawal if the deformed portions were in contact with the proximal housing 100a. The application of such applied larger forces when the deformed portions are in contact with a housing, could possibly cause the clinician to believe that there was a problem with the catheter or could cause the IV catheter to be withdrawn from the patient while the insertion stylet/sharp/cannula 20 is being pulled from the IV catheter.

Also, in the case where deformed portions are in contact with the proximal housing 100a, there is a potential that the septum 316g will not completely self-seal following removal of the insertion stylet/sharp/cannula 20. Typically, IV catheters are designed with a view towards an expectation of a shelf life on the order of years and in such a case the compressive forces could cause compressive set in the septum material thereby preventing the opening formed in the septum 316g for the insertion stylet/sharp/cannula 20 to fully close following removal. Consequently, there is a potential for blood leakage following removal of the insertion stylet/sharp/cannula 20.

Figure 10A:
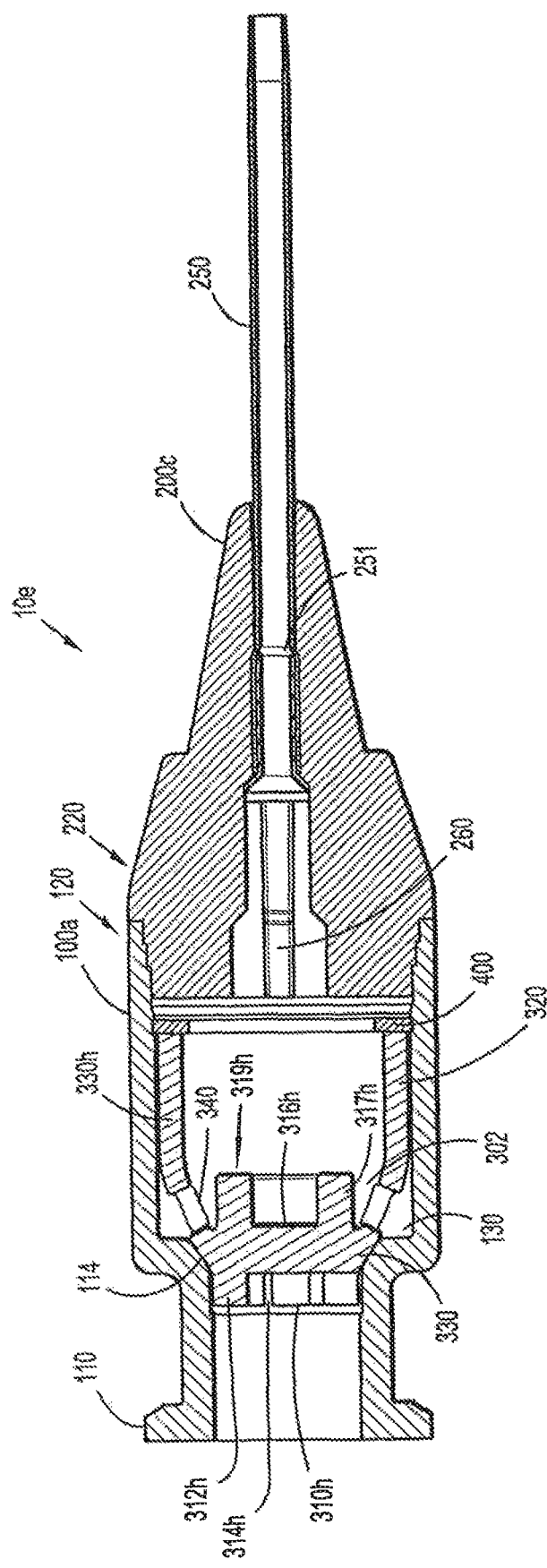
FIG. 10A is a cross-sectional view of an embodiment of said another in-line valve IV catheter of FIG. 9A in which the seal member embodies a co-planner septum which includes a collar portion.
Figure 10B:
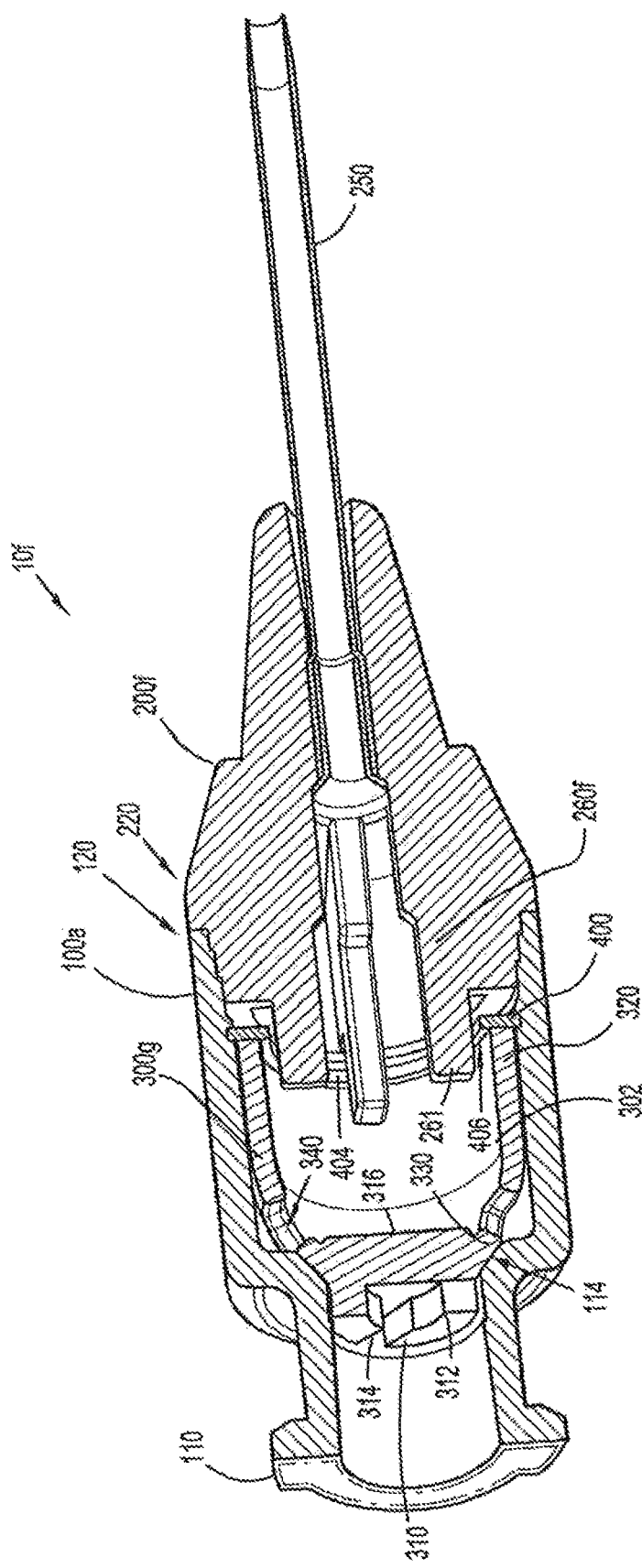
FIG. 10B is a cross-sectional view of an in-line valve IV catheter according to the present invention embodying another distal housing embodiment.

Referring now to FIG. 10A, there is shown a cross-sectional view of an embodiment of another in-line valve IV catheter 10e, which includes a seal member 300h that embodies a septum 316h that generally lies in the same plane as the sealing portion 330 (i.e., co-planar septum) and a collar portion 319h that extends outwardly from the co-planar septum. The insertion stylet/sharp/cannula 20 is not shown in this view for clarity; however, such an insertion stylet/sharp/cannula 20 would be disposed in the in-line valve IV catheter assembly 10e as shown in FIG. 2a so it passes through the planar septum 316h. Reference shall be made to the foregoing discussion regarding FIGS. 1-8 for details or characteristics regarding the proximal housing 100, the distal housing 200c, the ring member 400 and the seal member 300h not otherwise described or detailed below.

The seal member 300h of this embodiment includes a proximal end 310h, a distal portion 320, a sealing portion 330, an inner cavity 302 and one or more of windows 340 or through apertures. As to the proximal end 319h, this end includes one or more raised sections 312h arranged about a centrally positioned chamber 313h and one or more passages or channels 314h between each of the one or more raised sections 312h and which are fluidly coupled with the central chamber 313h. As herein described, the raised sections 312h and the channels 314h cooperate so that when the sealing portion 330 of the seal member 300h is displaced from the proximal housing seating surface 114, one or more flow paths are established with the centrally positioned chamber 313h thereby comprising a continuation of the fluid flow path through the in-line valve IV catheter 10e.

The proximal end 310h also includes a co-planar septum 316h and a side wall(s) 317h that extends axially outwardly from the co-planar septum 316h into the seal member inner cavity 320 thereof so as to form the collar portion 319h beneath the co-planar septum 316h. Thus, when the insertion stylet/sharp/cannula 20 is disposed in the in-line valve IV catheter assembly 10e it passes through the planar septum 316h and through the cavity into the inner cavity 320 of the seal member 300h.

Without being bound to any particular theory or principle of science, the collar portion 319h enhances the ability of the co-planar septum 316h to self-close or self-seal itself after the insertion stylet/sharp/cannula 20 is removed from the co-planar septum 316h. Also, the collar portion 319h enhances the ability of the septum 316h to limit or resist propagation of any tears that may originate in the co-planar septum 316h. These advantageous effects are attributed to the presence of the collar portion 319h and the effect such a structure has on enhancing or increasing the radial stiffness of the co-planar septum 316h.

Reference also should be made to the foregoing discussion regarding FIG. 9E as to the beneficial effects associated with such a septum collar portion.

Figure 11A:
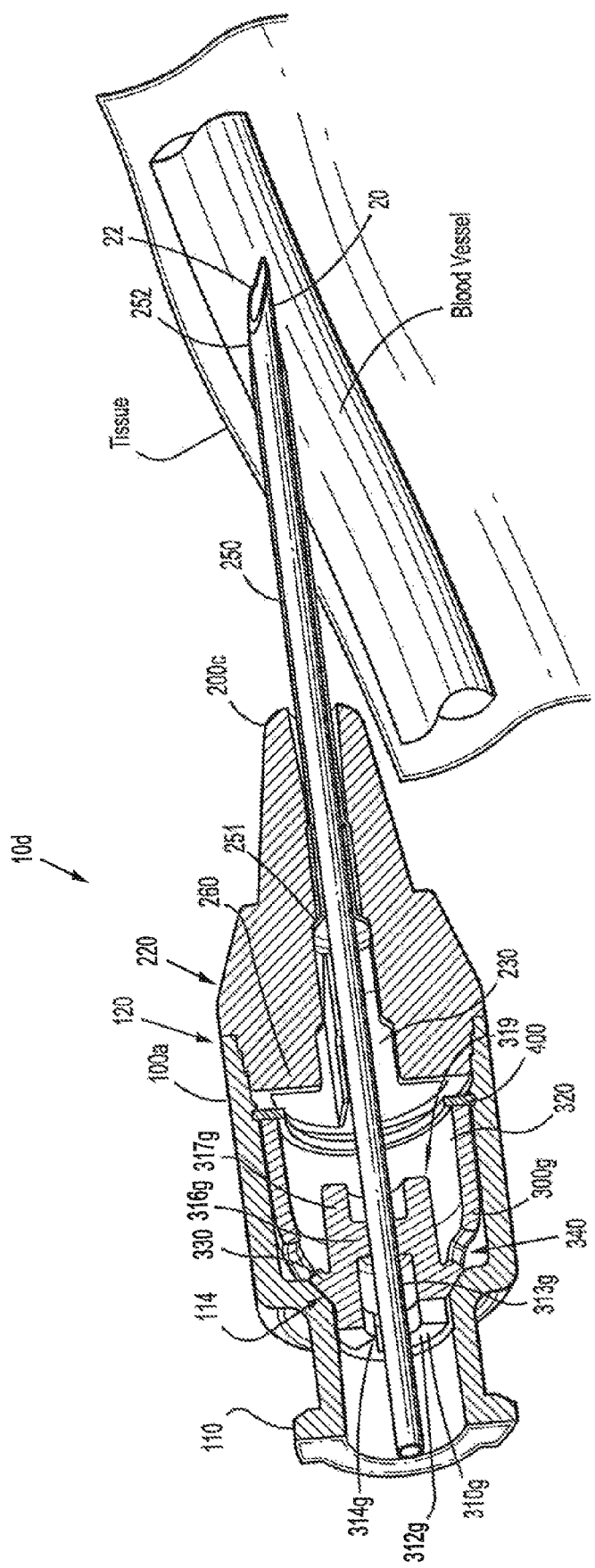
FIGS. 11A, B are cross-sectional views of the in-line valve IV catheter illustrating an exemplary use of such an IV catheter.
Figure 11B:
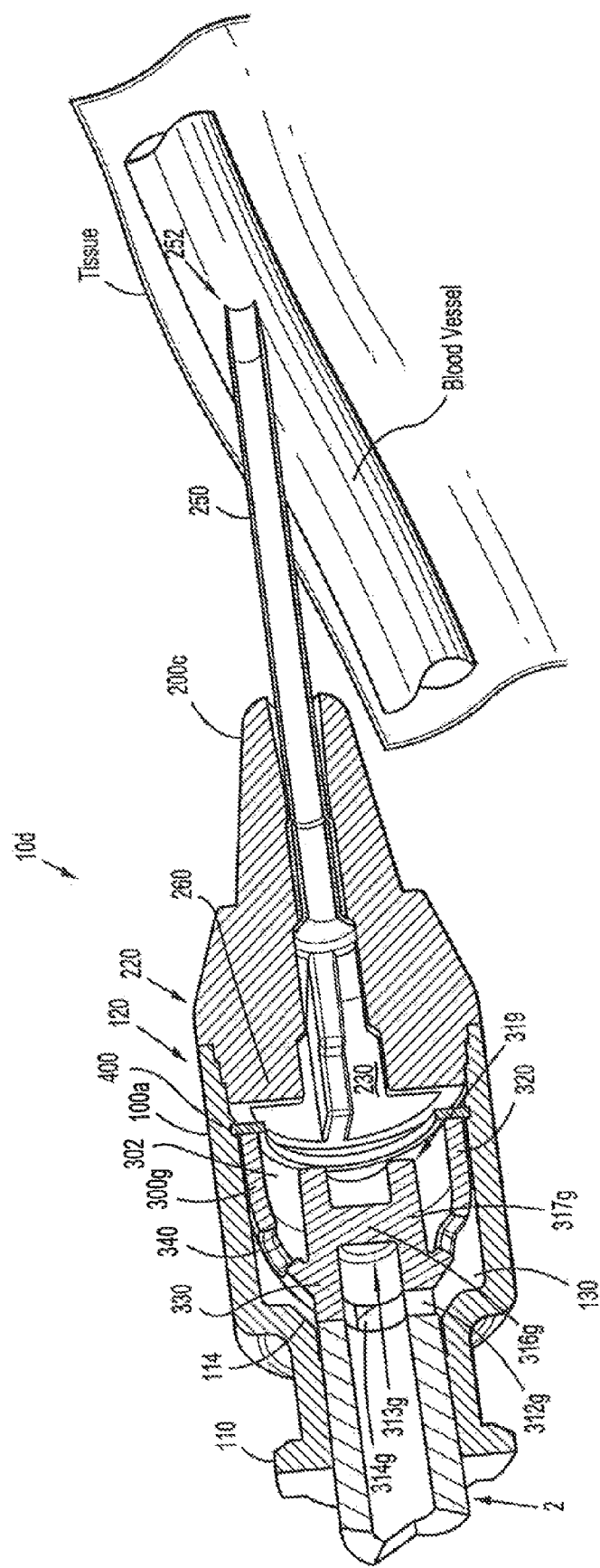
FIG. 11C is annotated cross-sectional view of the in-line valve IV catheter of FIG. 11B illustrating fluid flow in one direction when the sealing portion of the seal member is displaced responsive to the insertion of a nose of a luer device.
Figure 11C:
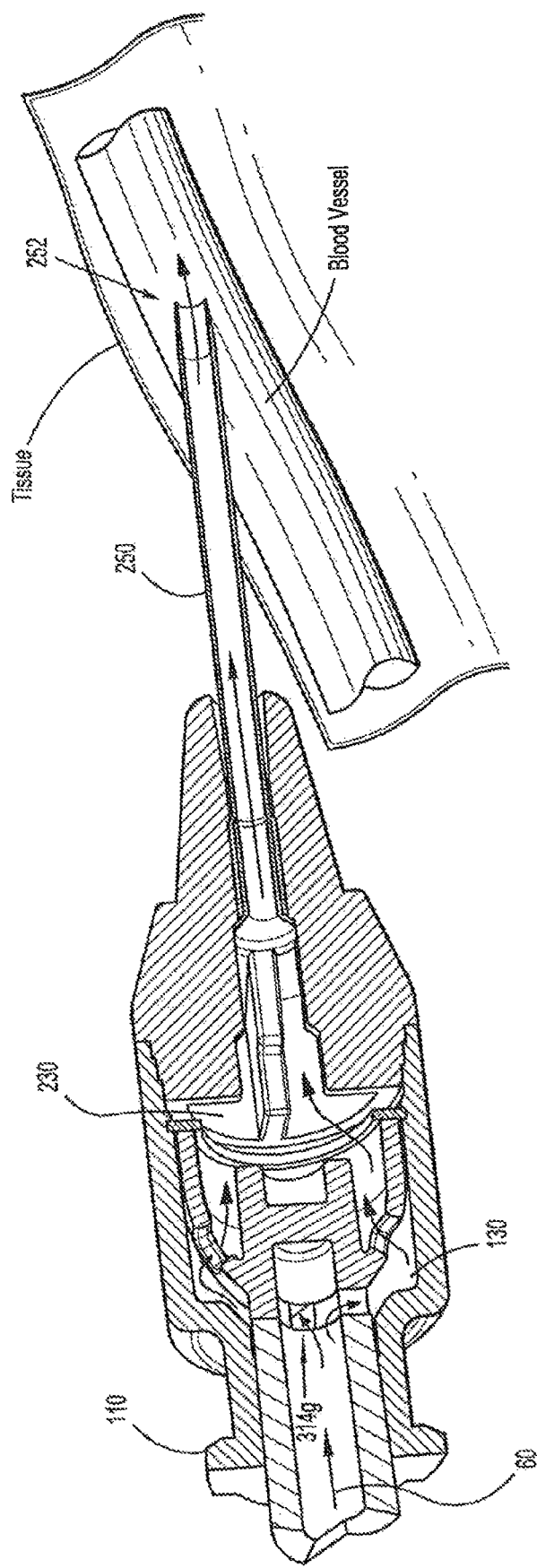

The use of an in-line valve IV catheter according to this aspect, can be best understood from the following discussion and with reference to FIGS. 11A-C. In this regard reference shall be made to the foregoing discussion regarding FIGS. 1-9 for details or characteristics regarding the proximal housing 100a, the distal housing 200c, the ring member 400 and the seal member 300g not otherwise described or detailed below. While the following discussion and figures utilize the in-line valve IV catheter 10d of FIGS. 9A-D, this shall not be construed as being limiting as any in-line valve IV catheter according to the teachings herein is useable as hereinafter described.

Figure 1A:
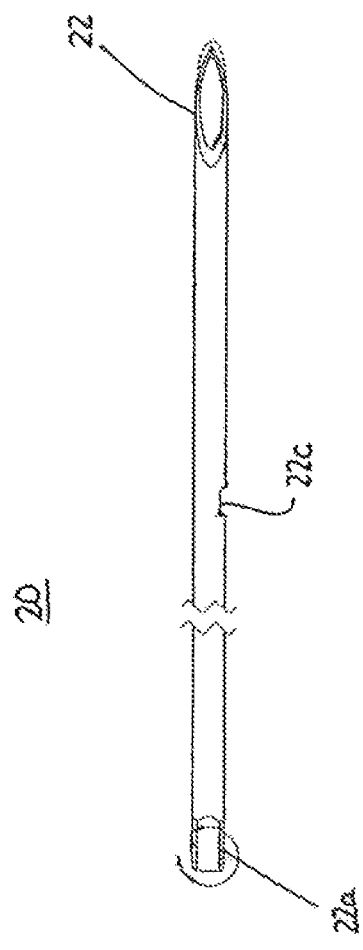
FIG. 1A is a side partial cross-sectional view of the stylet/sharp/cannula.
Figure 1B:
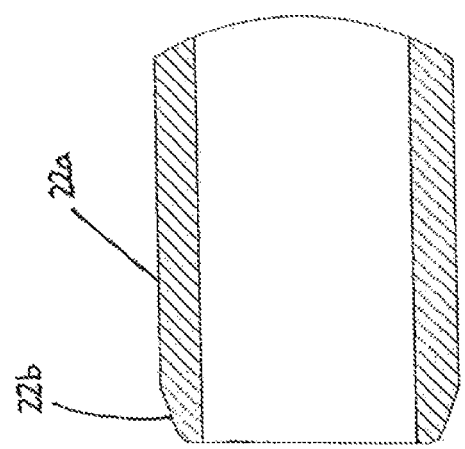
FIG. 1B is an enlarged view of the indicated area of detail shown in FIG. 1A.

An in-line valve IV catheter 10d of the present invention is typically assembled in a manufacturing facility and the assemblage is shipped to a storage facility, hospital, clinic, doctor's office or the like. As illustrated in FIG. 11A, the in-line valve catheter 10d is typically assembled so the introducer needle 20 or cannula is inserted into the IV catheter so it passes through the septum 316g and so the sharp tip or end thereof 22 extends from the open end of the tubular member 250. Referring also to FIGS. 1A and 1B, preferably introducer needle 20 has a proximal end 22a which includes a chamfer 22b. When the IV catheter is assembled at the manufacturing facility, the proximal end 22a of introducer needle 20 which is chamfered is inserted through the septum 316g of seal member 300h. By inserting the chamfered proximal end 22a of needle 20 through seal member 300 in a proximal direction, rather than inserting sharp distal end 22 through seal member 300 in a distal direction, damage to the seal member can be minimized. Thereafter, the distal housing portion 200c is secured to the proximal housing portion 100a, such as by sonic welding or other known fastening techniques, such that sharpened distal end 22 of needle 20 extends through catheter tubular member 250. In one embodiment, the seal member includes a releasable opening in septum 316, through which the proximal end 22a of the needle 20 is inserted through during assembly. As shown in FIG. 1A, the introducer needle can include structure such as a flashback chamber 22c operably coupled to the lumen in the introducer needle 20. The introducer needle and related structure also can further include a needle protection device, as is known to those skilled in the art, that protects the medical personnel from accidental needle sticks after the introducer needle is withdrawn from the in-line valve IV catheter.

Figure 12:
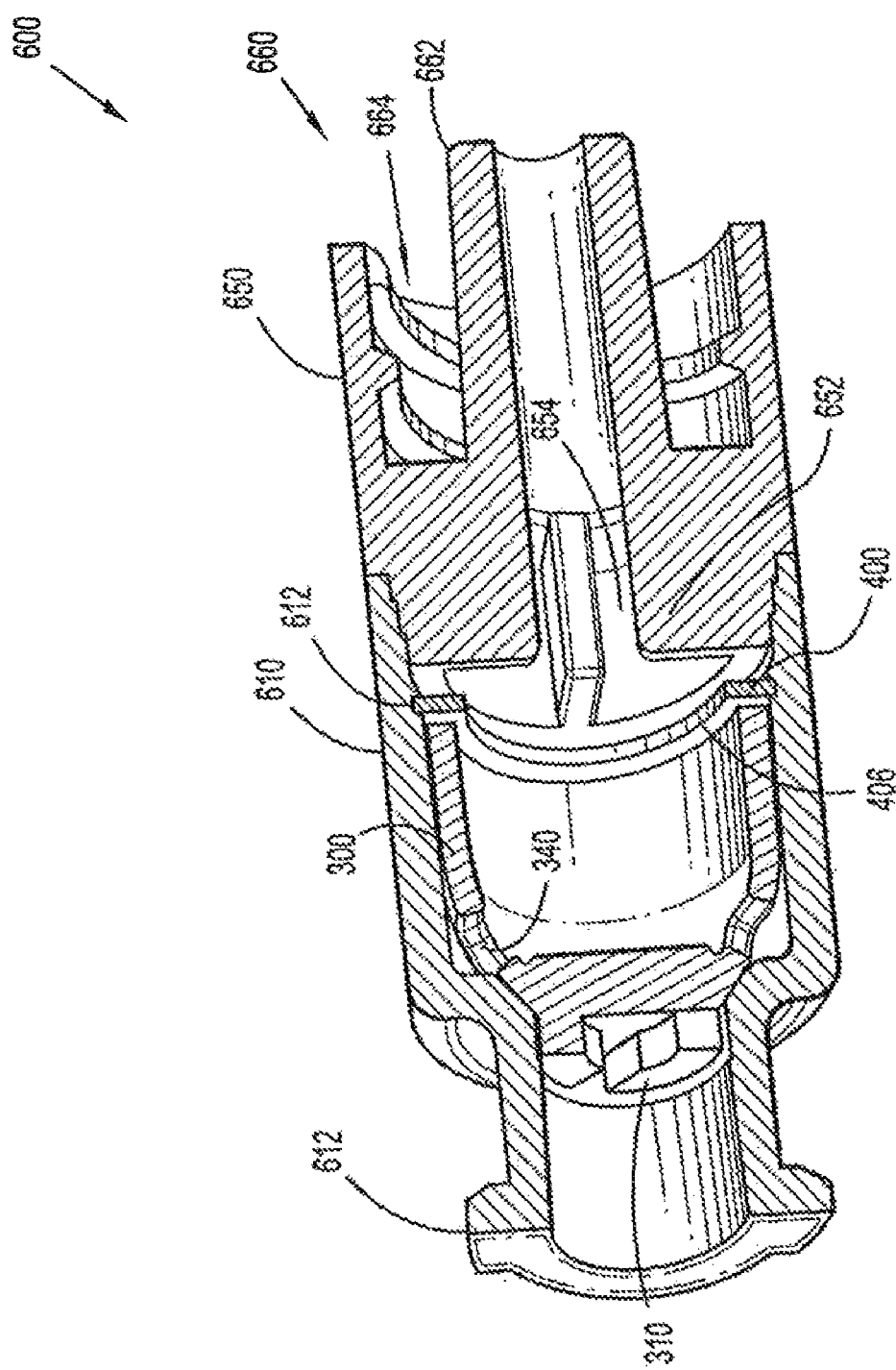
FIG. 12 is a cross-sectional axonometric view of an in-line valve device according to the present invention.

FIG. 12 illustrates an in-line valve connector 600 also referred to as a needleless connector, for use in fluid connection with medical application such as with intravenous lines. Unlike the embodiments described above, the in-line valve connector 600 does not include a tubular member. In-line valve connector 600 includes a proximal housing 610, a distal housing 650, seal member 300, ring member 400, and fins 652 defining flow channels 654. Proximal housing 610 includes a coupling end 612 and distal housing 650 includes a coupling end 664. Coupling ends 664 can include any of a number of connection devices or techniques including standard luer type connectors or the like. Distal housing 650 defines a tubular outlet 662 which communicates with an internal chamber. In use, coupling end 664 can be coupled to an IV line which may be attached to a catheter. A syringe or the like can be coupled to coupling end 612 of proximal housing 610 such that fluid can be injected into or withdrawn from in-line valve 600.

It should be noted that it is contemplated, and thus within the scope of the present invention, for the subject invention to further comprise device kits that include one or more the in-line valve IV catheters and which device kits maintain the in-line valve W catheter in sterile conditions during shipment from the manufacturing facility and in storage prior to use. Such device kits also can further include other instrumentalities, devices or materials normally associated with use of the catheter, including but not limited to tubing, cleaning materials to establish aseptic conditions prior to insertion of the IV catheter and/or clips/clamps or the like for regulating flow of fluid from an IV drip to the patient.

Initially, the medical personnel would prepare the in-line valve IV catheter 10d for use in accordance with the technique/procedure to be performed including removing the catheter from any device kit. The medical personnel would then perform the usual and customary actions to identify a potential target insertion site (e.g., locating a vein in which the open end of the tubular member 250 would be located) and to prepare the exposed skin of the patient surrounding the injection site for insertion of the needle into the patient's skin. Such preparing can include, for example, performing a cleaning and/or sterilizing operation (e.g., swabbing the skin with alcohol swab, applying a sterilizing solution).

Thereafter, the medical personnel would locate the sharp end 22 or point of the introducer needle 20 on the patient's body at the target insertion site. Following such localizing, the medical personnel would insert the sharp end 22 or point of the introducer needle 20 into and through the skin of the patient and the wall of the blood vessel such that the needle sharp end resides within the targeted blood vessel of the patient.

As indicated herein, once the sharp end 22 of the introducer needle 20 is in the blood vessel, the pressure of the blood within the patient causes blood to flow back or flashback in a proximal direction through the lumen in the introducer needle to the flashback chamber or a needle hub or space between the needle and catheter. In accordance with accepted practices, if the medical personnel observe such blood flashback in the flashback chamber, it is concluded that the open end of the tubular member also resides in the blood vessel. It should be noted that if the medical personnel do not observe such blood flashback, the medical personnel again attempt to insert the needle into the target vein and/or identify a new target vein and repeat to the extent necessary any of the foregoing steps (e.g., repeat the process if the new target vein is in another location or body part).

If it is determined that the needle end 22 is in the blood vessel/vein, the medical personnel then take the appropriate actions to remove the introducer needle 20 from the in-line IV catheter 10d. Typically, the medical personnel would grasp a handle, the flashback chamber or other mechanism of the related structure of the introducer needle 20 and draw the needle in a proximal direction thereby drawing the sharp end of the needle through and thence out of the in-line IV catheter. After the introducer needle 20 is removed from the in-line valve IV catheter 10*d*, the catheter remains positioned in the blood vessel (i.e., the open end thereof is within the blood vessel). It should be noted that after such removal or in conjunction with such removal, a needle end protection device can be actuated to protect users from the needle's sharp end 22, thereby preventing accidental needle sticks such as for example the safety shield devices described in PCT Publication No. WO (2005/042073, published May 12, 2005). In addition, the medical personnel can advance the in-line valve IV catheter 10*d* deeper into the vein by pushing gently on the coupling end 110 of the proximal housing 100 as the catheter is being advanced off the introducer needle 20.

As indicated herein, the in-line valve IV catheter 10*d* is in the valve closed condition when the catheter is inserted into the patient's body. As such, and as shown in FIG. 11A, a fluid seal or pressure boundary is formed between the seating surface 114 of the proximal housing 100*a* and the sealing portion 330 of the seal member 300. As also indicated herein, the septum 316*g* is self-sealing following removal of the introducer needle 20 from the septum. Consequently, when the introducer needle 20 is completely removed from the in-line valve IV catheter 10*d*, the fluid seal prevents blood from flowing through the IV catheter and out through the opening of the coupling connection 110.

At this point, the in-line valve IV catheter 10*d* is now positioned within the vein as a completely enclosed direct luer vascular access system ready to receive a luer end such as for a syringe or an IV tubing system. The in-line valve IV catheter 10*d* of the present invention thus allows immediate luer access to the blood vessel of the patient for infusion of medication or blood collection utilizing a blood collector having a luer tip as are known in the art.

In an illustrative embodiment and with reference to FIG. 11B, a male luer is attached to, or mates, with the coupling connection 110 of the proximal housing 100. The male luer mates with the luer attachment fitting comprising the coupling connection 110 by rotating the luer tapered fitting into the luer until recesses engage the luer attachment projections. The luer also includes a nose portion 2 that is inserted into the lumen or fluid passageway of the coupling connection. The inserted nose portion 2 also thereby contacts and engages the crown or raised portions 312*g* of the seal member 300 which extends into the lumen or fluid passageway of the coupling connection.

The engagement of the nose portion 2 with the raised portions 312*g*, along with the axial movement of the nose portion as the male luer is mated with and secured to the coupling connection 110, causes the proximal end 310 of the seal member 300 to move axially in a distal direction. Such axial movement also causes at least some of the sealing portion 330 of the seal member to be moved axially in a proximal direction thereby displacing the sealing portion from the proximal housing seating surfaces 114. Such displacement thus breaks the seal between the proximal housing seating surfaces 114 and the sealing portion 330 thereby creating the valve open condition and thereby also allowing fluid to flow through the in-line valve IV catheter.

Referring now also to FIG. 11C in which is shown an annotated cross-section view illustrating fluid flow in the distal direction, when the in-line valve IV catheter 10*d* is configured in the valve open configuration, fluid is free to flow from the coupling connection 110 through the channels 314*g* in the seal member proximal end 310, about the seal member 300 in a portion of the proximal housing inner cavity 130 and thence through the windows 340 of the seal member. The fluid continues to flow through the seal member inner cavity 302, through the aperture or opening in the ring member 400, through the distal chamber inner cavity 230, through the lumen in the tubular member 250 and thence into the blood vessel. The converse would apply if the fluid was to flow in the proximal direction such as in the case where fluid was being extracted from the blood vessel such as for sampling for diagnostic testing.

When the male luer is detached or decoupled from the coupling connection 110 of the proximal housing 100, the axial force displacing the sealing portion 330 of the seal member is no longer being applied to the seal member proximal end 310. As herein described, when the axial force is removed, the resiliency of the seal member 300 causes the proximal portion 310 thereof to move proximally and axially so as to cause the sealing portion 330 to again sealingly engage the seating surface 114 of the proximal housing. Thus, the in-line valve IV catheter 10*d* is restored or returned to the valve closed condition.

When the in-line valve IV catheter 10*d* is no longer needed, the medical personnel, using appropriate techniques' would remove the tubular member 250 from the blood vessel and tissues of the patient.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method for assembling an in-line IV catheter device comprising the steps of:
   providing a proximal housing portion defining an internal cavity, the proximal housing portion having a proximal end and a distal end;
   providing a distal housing portion defining an internal cavity, the distal housing portion having a proximal end and a distal end;
   providing a seal member having a proximal end, a distal end, and including a septum;
   positioning the seal member in the internal cavity of the proximal housing portion;
   providing a needle having a sharpened distal end and a proximal end;
   inserting the proximal end of the needle through the septum of the seal member such that the proximal end of the needle projects from the proximal end of the seal member; and
   securing the proximal housing portion to the distal housing portion such that the internal cavities of the proximal and distal housing portions define a chamber.

2. The method of claim 1, wherein the step of positioning the seal member in the internal cavity of the proximal housing portion includes positioning the seal member for movement within the internal cavity therein to selectively establish a flow path about the seal member.

3. The method of claim 1, wherein the step of positioning the seal member in the internal cavity of the proximal housing portion further includes the step of securing the distal end of the seal member to the proximal housing portion such that the seal member is sealingly and compressibly retained against a proximal end of the internal cavity of the proximal housing portion.

4. The method of claim 3, wherein the step of securing the proximal housing portion includes:
positioning a ring member on the proximal housing portion a predetermined distance from a proximal end of the internal cavity of the proximal housing portion; and
compressibly retaining the seal member between the proximal end of the internal cavity of the proximal housing portion and a surface of the ring member.

5. The method of claim 4, wherein the step of positioning a ring member includes positioning the ring member in a groove formed in the proximal housing portion.

6. The method of claim 4, wherein the step of positioning a ring member includes positioning a ring member formed as a raised rib extending at least partially about a circumference of the internal cavity of the proximal housing portion.

7. The method of claim 1, wherein the step of providing a seal member includes providing a seal member wherein the septum defines a re-sealable opening, and the step of inserting the proximal end of the needle through the septum includes inserting the proximal end of the needle through the re-sealable opening.

8. The method of claim 1, wherein the step of providing a seal member includes providing a seal member with an inner cavity and at least one through aperture extending between the inner cavity and an outer surface of the seal member.

9. The method of claim 8, wherein the step of positioning the seal member includes positioning the seal member in the internal cavity of the proximal housing portion such that the at least one through aperture is positioned proximally of the proximal end of the internal cavity of the proximal housing portion such that the inner cavity of the seal member is fluidly coupled to the internal cavity of the distal housing portion after the proximal and distal housing portions are secured to each other.

10. The method of claim 1, wherein the step of providing a distal housing portion includes providing a distal housing portion with one or more radially extending fins positioned to limit axial travel of the seal member when the seal member is exposed to a high pressure fluid flow condition.

11. A method for assembling an in-line IV catheter device comprising the steps of:
providing a housing defining a chamber;
securing a tubular member to the housing such that a lumen extending though the tubular member is in fluid communication with the chamber;
positioning a seal member including a septum within the chamber of the housing such that the seal member is movable between a first position, wherein the seal member sealingly engages a region of the housing, and a second position, wherein the seal member permits fluid flow through the housing;
positioning stop structure within the housing such that the stop structure is spaced apart from the seal member when the seal member is in the first position, and the stop structure is configured, dimensioned, and positioned for engagement with the seal member when the seal member is in the second position to inhibit continued axial movement of the seal member; and
inserting a proximal end of a needle through the septum of the seal member such that the proximal end of the needle projects from a proximal end of the seal member.

12. The method of claim 11, wherein the step of positioning a seal member includes positioning the seal member such that the seal member is movable within the chamber of the housing to selectively establish a flow path through the housing about the seal member.

13. The method of claim 11, wherein the step of positioning a seal member includes positioning the seal member such that the seal member is moved from the first position to the second position upon realization of a predetermined level of pressure within the housing while maintaining fluid flow through the housing.

14. The method of claim 11, wherein the step of positioning stop structure includes positioning stop structure including at least one axially extending fin extending inwardly from an inner surface of the housing.

15. The method of claim 14, wherein the step of positioning stop structure includes positioning stop structure including at least one axially extending fin arranged so as to only contact the seal member during a high pressure fluid flow condition.

16. The method of claim 14, wherein the step of positioning stop structure includes positioning stop structure including at least one axially extending fin extending radially inward into the chamber of the housing.

17. The method of claim 14, wherein the step of positioning stop structure includes positioning stop structure including at least one axially extending fin configured, dimensioned, and positioned to inhibit inversion or folding of the seal member in response to increased pressure within the chamber.

18. The method of claim 14, wherein the step of positioning stop structure includes positioning stop structure including at least one axially extending fin extending inwardly into the chamber of the housing in a non-radial fashion.

19. The method of claim 14, wherein the step of positioning stop structure includes positioning stop structure including a plurality of axially extending fins that are spaced apart to provide an opening extending axially through the chamber of the housing, the opening being configured and dimensioned to receive an introducer needle.

20. The method of claim 13, wherein the step of positioning stop structure includes positioning stop structure distally of the seal member.

* * * * *